United States Patent [19]

Meruelo et al.

[11] Patent Number: 6,150,414

[45] Date of Patent: Nov. 21, 2000

[54] COMPOSITIONS AND METHODS FOR TREATING VIRAL INFECTIONS

[75] Inventors: Daniel Meruelo, Scarborough; Gad Lavie, New York, both of N.Y.; Yehuda Mazur, Rehovot, Israel

[73] Assignees: New York University, New York, N.Y.; Yeda Research and Development Co. Ltd., Rehovot, Israel

[21] Appl. No.: 07/970,229

[22] Filed: Nov. 2, 1992

Related U.S. Application Data

[63] Continuation of application No. 07/883,799, Feb. 15, 1992, abandoned, which is a continuation of application No. 07/488,518, Feb. 27, 1990, abandoned, which is a continuation-in-part of application No. 07/417,163, Oct. 4, 1989, abandoned, which is a continuation-in-part of application No. 07/324,177, Mar. 16, 1989, abandoned.

[51] Int. Cl.⁷ .............................. A01N 37/10; A01N 35/00
[52] U.S. Cl. ............................................. 514/569; 514/680
[58] Field of Search ...................................... 514/569, 680

[56] References Cited

U.S. PATENT DOCUMENTS

| | | | |
|---|---|---|---|
| 2,707,704 | 5/1955 | Brockmann et al. | 204/158 |
| 3,974,186 | 8/1976 | Fleming et al. | 260/380 |
| 4,670,265 | 6/1987 | Sydiskis et al. | 424/195.1 |
| 4,898,891 | 2/1990 | Lavie et al. | 514/732 |

FOREIGN PATENT DOCUMENTS

| | | | |
|---|---|---|---|
| 2044231 | 2/1975 | Japan | A01N 09/24 |

OTHER PUBLICATIONS

Lavie et al 109 CA: 32109 C 1988.
Meruelo et al. 109 CA: 104223K 1988.
Merch Index 10$^{th}$ ed #4786.
Rodewald, G. et al., "Synthesis of Hyericin and Related meso–Naphthodianthrones by Alkaline Dimerization of Hydroxyanthraquinones", *Angew. Chem. Int. Ed. Engl.* 16(1):46 (1977).
Banks, H.J. et al., Chemistry of the Coccoidea. II Condensed Polycyclic Pigments from Two Australian Pseudococcids (Hemiptera), *Aust. J. Chem.* 29:1509–21 (1976).
Cameron, D.W. et al., "Pseudohypericin and Other Phenanthroperylene Quinones", *Aust. J. Chem.* 29:1523–33 (1976).
Spitzner, D., "Synthesis of Protohypericin from Emodin", *Angew. Chem. Int. Ed. Engl.* 16(1):46 (1977).
Brockmann, H. et al., "Zur Kenntnis Des Hypericins und Pseudo–Hypericins", *Chem. Ber.* 90:2480 (1957).
Brockmann, H. et al., "Die Konstitution des Hypericins", *Chem. Ber.* 84:865 (1951).
Weiss et al. "Naturally Occurring Perylenequinones", *Progress in Chemistry of Organic Natural Products*, 52: 1–71 (1987).

*Primary Examiner*—Marianne M. Cintins
*Attorney, Agent, or Firm*—Browdy and Neimark

[57] ABSTRACT

Disclosed herein are antiviral agents, pharmaceutical formulations comprising effective amounts of these agents and methods for treating mammals suffering from infections caused by viruses. The agents are analogs, isomers, homologs, derivatives and salts of aromatic polycyclic diones.

2 Claims, No Drawings

COMPOSITIONS AND METHODS FOR TREATING VIRAL INFECTIONS

CROSS-REFERENCE TO RELATED APPLICATIONS

This application is a continuation of 07/883,799 filed May 15, 1992, now abandoned which is a continuation of application Ser. No. 07/488,518, filed Feb. 27, 1990, now abandoned, which in turn was a continuation-in-part of application Ser. No. 07/417,163, filed Oct. 4, 1989, now abandoned, which in turn was a continuation-in-part of application Ser. No. 07/324,177, filed Mar. 16, 1989, now abandoned.

This application is a continuation-in-part of copending U.S. patent application Ser. No. 324,177, filed Mar. 16, 1989.

BACKGROUND OF THE INVENTION

This invention relates to antiviral compounds, compositions and pharmaceutical formulations comprising effective amounts of these compounds and methods for treating or preventing infections caused by viruses in mammals.

The ability of viruses to invade cells and parasitize cellular biochemical mechanisms for viral replication restricts the potential means and methods that can be used to selectively inhibit such replication. Very few antiviral agents which are non-toxic for non-infected cells are known. Furthermore, most antiviral agents are of limited effectiveness.

Retroviruses are particularly elusive targets for antiviral agents precisely because these viruses differ radically in their mode of replication from the DNA-containing and other RNA-containing viruses. Retroviruses become integrated into the cellular genome and their replication is probably mediated by cellular enzymes. This severely restricts the possibilities of eliminating the virus from the host cell. Only a few compounds are known to possess relatively selective (i.e. relatively noncytotoxic) anti-retroviral activity. The nucleoside analog 3'-azido-3'-dideoxythymidine also commonly known as azidothymidine (hereinafter referred to as AZT) and other nucleoside analogs (such as the dideoxycytidine analog of cytosine) owe their relative selectivity for virally-infected cells to their ability to inhibit retroviral functions (i.e., the activity of reverse transcriptase enzyme) more efficiently than they inhibit host cell functions (i.e., the activity of DNA polymerase). The use of such nucleoside analogs is limited due to their narrow spectrum of activity and their toxic side-effects when administered systemically to a host organism over long periods of time. Furthermore, long-term use of these drugs increases the likelihood of development of resistant mutants.

A member of the retroviral family, the Human Immunodeficiency Virus (HIV), is currently being spread in epidemic proportions in the U.S. and around the world. HIV is now believed to be the causative agent of Acquired Immune Deficiency Syndrome (AIDS). Two different serotypes of the virus have been identified to date: HIV-1 and HIV-2. Current estimates are that approximately 1.5 million people have been infected with HIV at this time in the United States alone. It is believed that the vast majority of individuals infected with the virus eventually will develop AIDS and are likely to succumb to opportunistic infections and/or malignancies.

The drug currently used against HIV infection is AZT. However, because of the toxicity of AZT and because its effectiveness is also otherwise limited, alternative antiviral agents (or at least agents of relatively low toxicity that could be used in conjunction with AZT therapy) are needed. Moreover, because of its toxicity, AZT is inappropriate for use prophylactically and therefore less toxic alternatives suitable for prophylactic use are desired. In addition, AZT-resistant strains of HIV have been recently reported.

Copending U.S. patent application Ser. No. 082,700 of D. Lavie et al. filed Aug. 7, 1987, discloses the antiviral activity of two aromatic polycyclic dione compounds: hypericin (Hy) and pseudohypericin (Ps).

Copending U.S. patent application Ser. No. 084,008 of D. Lavie et al. filed Aug. 10, 1987 expands upon the disclosure of U.S. application Ser. No. 82,700, now U.S. Pat. No. 4,898,891 focusing on the use of Hy and Ps as effective anti-retroviral agents.

Copending U.S. patent application Ser. No. 172,064 filed Mar. 23, 1988 of D. Meruelo et al. discloses anti-retroviral compositions comprising effective amounts of Hy and Ps in combination with nucleoside analogs such as AZT and methods for treating retroviral infections.

In addition, copending U.S. patent application of Daniel Meruelo and Gad Lavie Ser. No. 299,971, filed Jan. 19, 1989 entitled Blood Purification System discloses compositions and methods for inactivating viruses and retroviruses present in blood, other body fluids and, more generally biological fluids, and articles used in the practice of such methods. The compositions comprised hypericin, pseudo-hypericin, isomers, analogs, homologs, and derivatives of aromatic polycyclic diones and mixtures of these compounds, all of which are also used in the present invention.

The present invention is directed to use of a variety of compounds structurally related to hypericin as therapeutic (or prophylactic) antiviral and antiretroviral agents in vivo.

Therefore, it is an object of the present invention to provide novel therapeutic agents for the treatment (or prevention) of viral infections. (Henceforth, the terms "virus" and "viral" will include "retrovirus" and "retroviral" unless explicitly stated otherwise.)

Another object of the present invention is to provide methods for treating mammals suffering from (or potentially exposed to) infections caused by viruses, especially HIV.

A further object of the present invention is to provide pharmaceutical formulations for treating individuals suffering from (or potentially exposed to) viral infections.

These and other objects of the present invention will be apparent to those of ordinary skill in the art in light of the present description accompanying drawings and appended claims.

SUMMARY OF THE INVENTION

The present inventors have discovered that certain compounds are effective for treating or preventing viral infections in mammals. Furthermore, the present inventors have devised compositions (comprising such compounds) suitable for therapeutic or prophylactic use in vivo. These compounds are related to hypericin and comprise monomers or diners of anthracenes, anthraquinones and anthrones, as well as homologs, isomers, derivatives, salts and analogs of any of the foregoing and mixtures thereof. (Hereafter, these compounds will be referred to as "antiviral anthraquinone- or anthracene- or anthrone-based compounds" abbreviated as "AAB".) In addition, within the scope of the present invention are various aromatic polycyclic dione compounds as well as homologs, isomers, derivatives, salts and analogs of such polycyclic compounds and mixtures thereof.

Hereafter, all the compounds of the present invention including those which are not "AAB compounds" will be referred to collectively as "polycyclic antiviral compounds" or "PAC". In this context, "polycyclic" means having at least three rings.

In one aspect, the present invention comprises a method for preventing or treating a viral infection in a mammal comprising administering to such a mammal an effective amount of a compound selected from the group consisting of PAC compounds and mixtures thereof wherein said PAC compounds or mixtures are used as the sole antivirally active ingredients or in conjunction with other antiviral agents (or in conjunction with stabilizers and/or potentiators of PAC compounds and/or other antiviral agents).

Another aspect of the present invention comprises pharmaceutical compositions and formulations for treating or preventing viral infections in mammals, said compositions and formulations comprising an effective amount of an antiviral agent selected from the group consisting of PAC compounds and mixtures thereof and a pharmaceutically acceptable carrier or diluent.

DETAILED DESCRIPTION OF THE INVENTION

All patents, patent applications and literature references referred to in this specification are hereby incorporated by reference in their entirety. However, the meaning specifically ascribed herein to defined terms shall prevail (in case of discrepancy with definitions in the prior patent applications incorporated by reference herein).

The present inventors have discovered that PAC compounds are useful for the treatment (or prevention) of infections caused by viruses.

The structure of the AAB compounds and many PAC compounds falls within the general Formula I

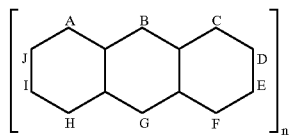

(I)

wherein: n is an integer selected from 1 and 2;
each of A, C, D, E, F, H, I, J is independently selected from the group consisting of hydrogen, hydroxy, lower ($C_1$–$C_4$) alkyl, aryl, arylalkyl, arylamino, lower alkenyl, alkoxy, hydroxyalkyl, halogen, carboxy, acyl (aromatic or aliphatic), amino, acyloxy, alkoxycarbohyl, aryloxycarbonyl (each of which may be substituted or unsubstituted), and a dimer-forming bond;
each of B and G are independently selected from the group consisting of (a) oxygen forming a keto group with the ring carbon to which the oxygen is appended; (b) two hydrogen atoms; (c) one hydrogen atom and one peroxy group; (d) aryl; (e) alkenylcarbonylalkyl; (f) alkenyloxycarbonylalkyl; (g) cyanoalkenyl; (h) arylalkenyl; (i) lower alkyl; (j) alkenyl; (k) acyl; each of which may be substituted or unsubstituted; and (l) a double or single dimer-forming bond;
wherein one or more of A and B, B and C, A and J, C and D, D and E, E and F, F and G, G and H, H and I, and I and J can be combined to form aromatic, alicyclic or heterocyclic rings having 5–7 carbon atoms, said rings optionally being further substituted;
wherein the three rings in said formula are aromatic except that the particular bonds formed by one or more of the ring carbon atoms adjacent to A, B, C, H, G or F can be saturated;
provided that, when n=2, at least one of H, G and F or at least one of A, B and C is a bond and either or both of (i) D and E and (ii) J and I optionally form aromatic or alicyclic or heterocyclic rings having 5–7 atoms with the adjacent carbon atoms.

Several of the compounds encompassed by the above formula can be considered monomers or dimers of substituted or unsubstituted anthracenes, anthraquinones, or anthrones.

For example, hypericin and substituted hypericins (such as hypericin hexaacetate) can be considered as dimers of anthraquinone (and substituted anthraquinones) with all the intermediate rings fused (i.e. wherein both H and F are single, dimer-forming, bonds and simultaneously G is a double, dimer-forming, bond). See compounds 7–10 (Series C) in Example 2 as well as compounds XI, XIV, XV, XVII.

For example, compound XX in Example 2 described in Brockmann in *Tetrahedron Letters,* infra, is a dimer of 1, 3, 8 trihydroxy-6-hydroxyethyl-9 anthrone wherein H G and F are all bonds; compound XXII is a dimer of 1, 3, 8 trihydroxy-6-methyl-9-anthrone wherein E has formed an extra ring with the corresponding side-chain of the second anthrone monomer.

Also within the definition of the PAC compounds are isomers, homologs, analogs, derivatives and salts of the compounds of Formula I.

"Homologs" shall mean compounds with structural formulas that differ from the compounds of Formula I (or from another PAC compound) by one or more carbon atoms and one or more hydrogen atoms or pairs of hydrogen atoms (see by way of non-limiting example, compounds XV and XVI of Example 2 below; see also the three pairs of compounds in the table of compounds synthesized according to U.S. Pat. No. 2,707,704 of Brockmann et al. issued May 3, 1955 of Example 2 below and visualize their homologs wherein one or more of the R groups will have been replaced by $C_2$–$C_4$ alkyl groups; and compare the structure of hypericin with that of protohypericin in Example 2 (Series C) below, etc.).

"Isomers" shall mean compounds having the same molecular formula as the compounds of Formula I (or another PAC compound) and shall include, without limitation, structural isomers, enantiomers, position isomers, optical isomers and stereoisomers (e.g. cis and trans, +and –, d and l) (see, by way of non-limiting example, compound 17 in Example 2 below of Banks et al. infra and its isomer wherein, e.g. the hydrogen atoms in the center would be oriented both below or above the plane of the paper and compound 25 in Example 2 below of Weiss, U. et al., infra which has several asymmetric carbon atoms and its various optical isomers).

"Analogs" shall include polycyclic aromatic compounds having the same activity as Hy and Ps (e.g., compounds referenced to Weiss, U. et al. infra, and compounds selected among compounds 1–36 of Example 1).

"Derivatives" shall include compounds bearing a strong structural similarity to a compound of Formula I or to another PAC compound but having one or more substitute groups in one or more positions (see, e.g. compounds 7 and 9 of Banks et al. in Example 2; benzoic acid derivatives of the XIX compound of Brockmann, et al., infra in Example 2 (series A) below and hydroxylated, esterified, alkyl-substituted and otherwise substituted derivatives of the compounds specifically disclosed herein). A non-limiting list of the compounds used in the present invention is set forth in Examples 1 and 2 below.

Salts (of the above compounds) soluble in aqueous media and physiologically acceptable are particularly preferred. "Salts" shall mean both complex salts (such as compound 26 of Weiss et al. infra of Example 2 below) and ionic salts.

The AAB dimer compounds can be synthesized using for example one of the synthetic schemes set forth below:

(Scheme I)

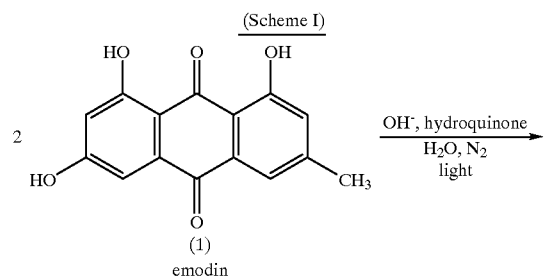

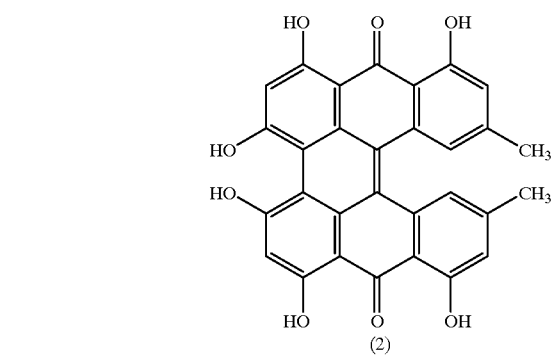

(Scheme II)

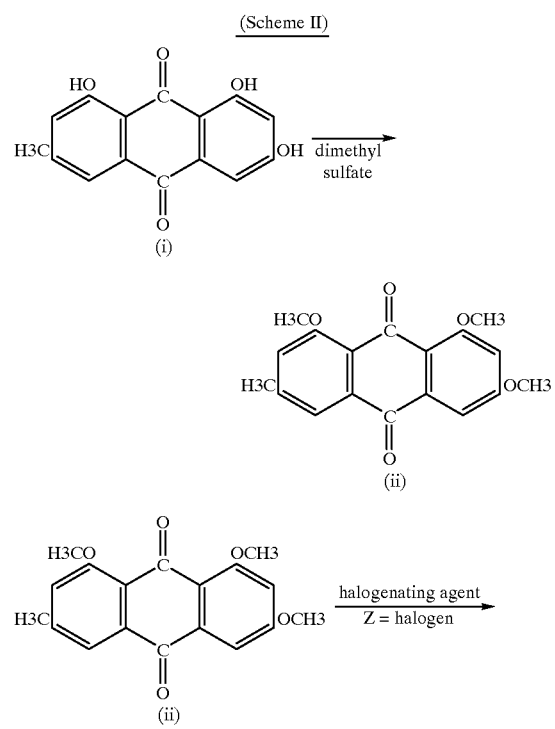

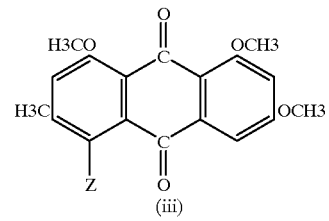

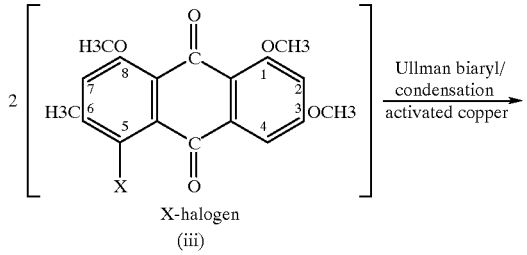

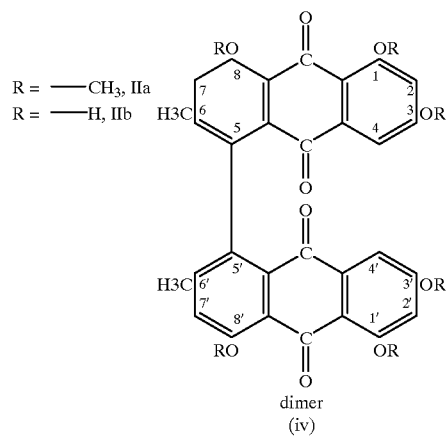

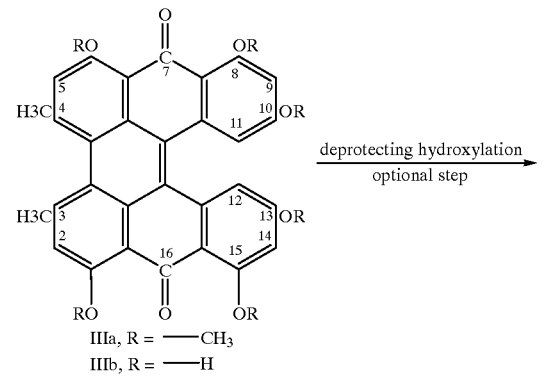

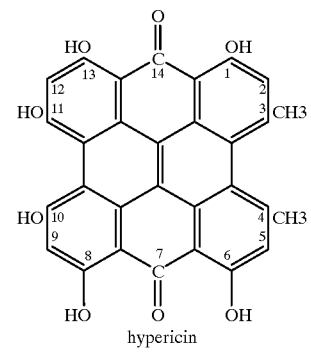

hypericin

This scheme also applies when the starting material is an anthracene or an anthrone.

The protecting/deprotecting step in Scheme I can be used or not depending on the starting material and the desired product (e.g. if the starting material is a fully alkoxylated emodin derivative such as compound 1 of the Brockmann patent, infra, and the end product is compound 7 of the same reference then no protection would be necessary). The various substitutes of the ultimate dimer can thus be appended either on the starting tricyclic (or other) material or can be constricted by modification of the dimeric structure itself, depending on the reactivity of each particular site, as is well-known in the art.

A third general reaction scheme is the following:

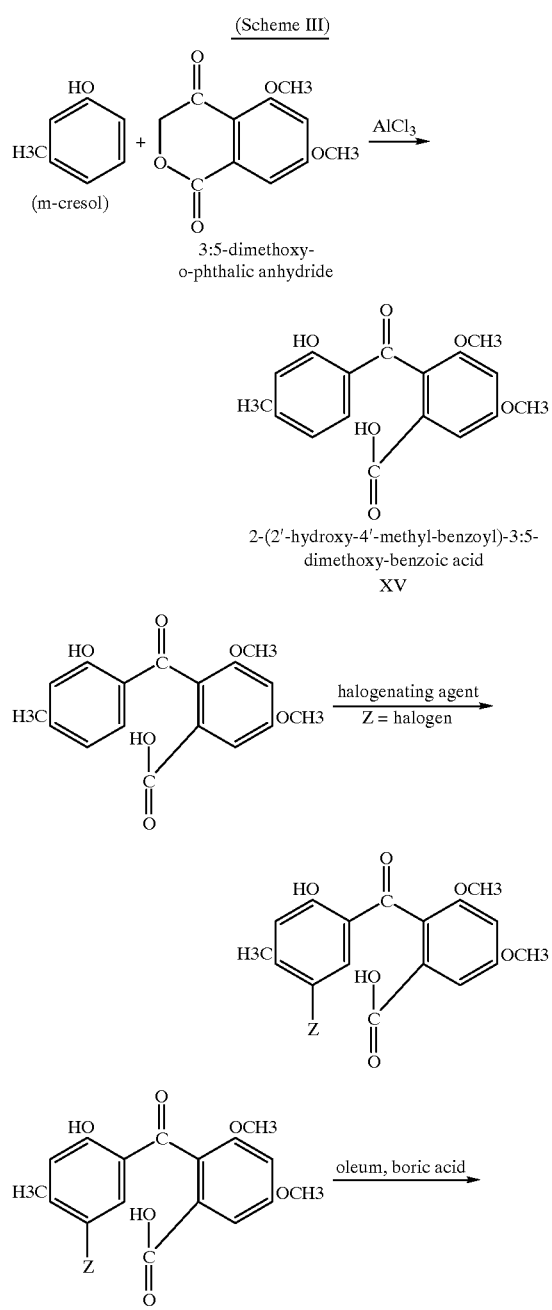

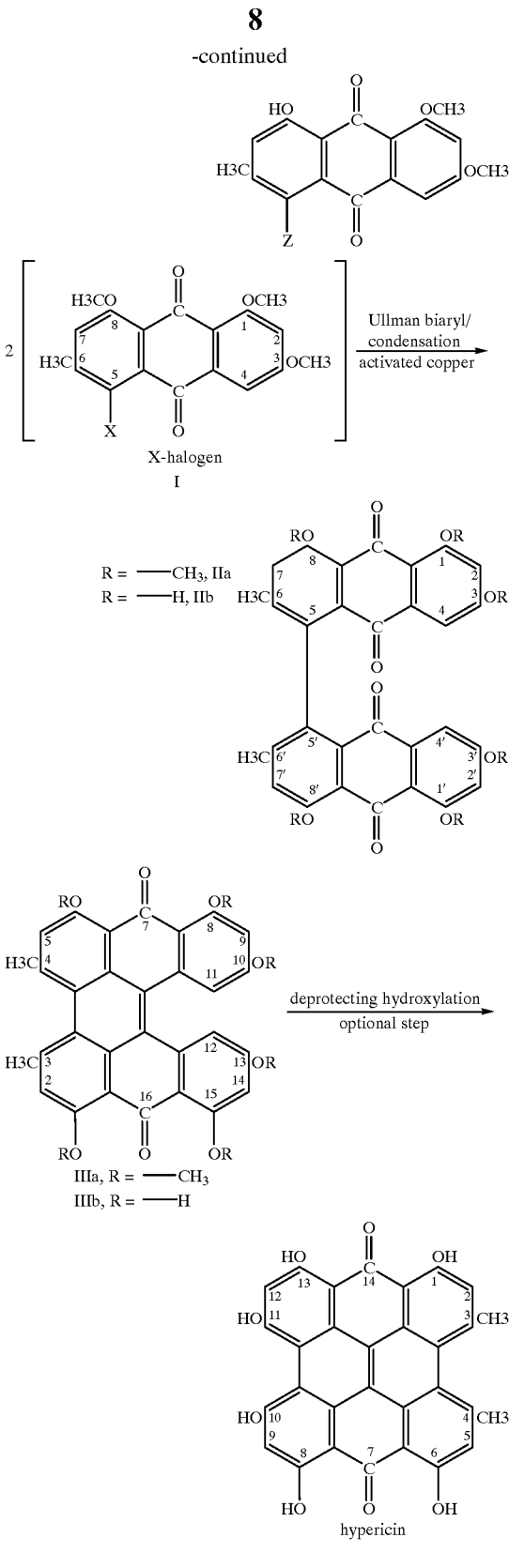

The starting monomers can be synthesized according to well-known techniques or can be purchased from commercial sources. For example, anthrone can be synthesized as described in *Org. Syn. Coll.* 1: 60, 1941, or purchased from Aldrich Chemical Co., Milwaukee, Wis. (Cat # A9,120-5).

Anthrone derivatives can be synthesized from anthrone as described in *Anal. Biochem.* 68:332, 1975.

Anthracene can be synthesized according to the method described in E. Clar, *Chem. Ber.* 72: 1645, 1957 and E. Clar, *Polycyclic Diones,* Academic Press, N.Y. 1964 or purchased from Aldrich Chemical Co, Cat. # A8, 922-0. Anthracene derivatives (such as anthracene dione) can be synthesized from phthalic acid and benzene in $AlCl_3$ via Friedel-Crafts reaction as described in *Ind. Eng. Chem.* 18: 1327, 1926.

In addition, PAC compounds can be advantageously combined (as therapeutic or prophylactic agents) with nucleoside analogs such as AZT when treating retroviral infection. That is, one or more PAC compounds can be administered in conjunction with one or more of AZT or another nucleoside analog. "In conjunction" includes co-administration, contemporaneous administration of different preparations (each preparation containing one type of active ingredient or ingredients—nucleoside(s) or PAC compound(s)—or alternating administration of nucleoside therapy and PAC compound therapy. Advantages of such conjunctive therapy include at least additive enhanced therapeutic (or prophylactic) effect—nucleoside therapy does not interfere with PAC therapy—and diminished risk of undersirable side-effects of either active ingredient. Preferred conjunctive therapy includes use of AZT and hypericin.

AZT is currently being employed to treat patients with AIDS and/or ARC (AIDS Related Complex, a prodrome of AIDS). AZT has been shown to improve immunologic functions, to reverse, at least partially, HIV-induced neurological disfunction in some patients and to improve certain other clinical abnormalities associated with AIDS. However, a dose-dependent suppression of bone marrow, resulting in anemia and leukopenia (an abnormally low number of leukocytes in the circulating blood) has been found to occur with its use. This has limited the effectiveness of AZT for the treatment of AIDS. Because of the displayed additive therapeutic or prophylactic effect of AAB and other PAC compounds administered in conjunction with AZT it is anticipated that it will be possible to use smaller doses of AZT for antiviral therapy when AZT is used in combination with the present compounds (most notably in AIDS therapy) which will decrease or eliminate the undersirable side-effects of AZT.

The combined effect of AZT and the compounds of the present invention is shown in Example 1 below. As illustrated in Example 1, the activity of AZT does not interfere with that of PAC compounds.

Accordingly, the present invention includes the use of effective amounts of PAC compounds (as disclosed below) in combination with AZT or other nucleoside analogs for treating viral (especially retrovival) infections. Non-limiting examples of nucleoside analogs useful in the present invention are 2', 3'-dideoxycytidine, 2', 3'-dideoxyadenosine, 2', 3'-dideoxythymidine and preferably azidothymidine (AZT, commercially available from Burroughs Welcome Research Triangle Park, N.C.). 2', 3'-dideoxycytidine and 2', 3'-dideoxyadenosine are commercially available from Calbiochem-Behring (San Diego, Calif.); 2', 3'-dideoxythymidine is commercially available from Pharmacia Fine Chemicals (Piscataway, N.J.).

The PAC compounds of the present invention (even when used by themselves, i.e., not in conjunction with nucleoside analogs) have a wide spectrum of effectiveness in inhibiting viruses and are especially effective in inhibiting enveloped viruses. Enveloped viruses are defined herein as viruses (both RNA- and DNA-containing) having a lipid-containing membrane. The lipid is derived from the host cell whereas the membrane proteins and glycoproteins are virally encoded. Non-limiting examples of the enveloped viruses which are inhibited by the compounds of the present invention are cytomegalovirus, Herpes Simplex Virus (HSV), vaccinia virus, influenza virus, Vesicular Stomatitis Virus (VSV), Hepatitis B virus and retroviruses.

Retroviruses are viruses containing an RNA genome and RNA-dependent DNA polymerase (reverse transcriptase) enzymatic activity. All retroviruses have common morphological, biochemical and physical properties that justify their inclusion into a single virus family. These parameters are summarized in Table I below (*RNA Tumor Viruses,* Weiss, R. et al. eds., p.28, Cold Spring Harbor Press, New York, 1984).

Most preferred among the AAB compounds are hypericin, pseudohypericin, hypericin hexaacetate, and protohypericin, with hypericin being the most active. For prophylactic administration the AAB compounds having low toxicity (by comparison to AZT) are preferred, with hypericin, pseudohypericin and protohypericin being again most preferred. In general, a compound is considered to have low toxicity if it has a therapeutic index greater than 5, i.e. it is effective at doses five times smaller than the dose at which it causes severe toxicity.

TABLE I

GENERAL PHYSICAL PROPERTIES OF KNOWN RETROVIRUSES

| | |
|---|---|
| Nucleic acid | linear positive-sense single-stranded RNA (60S–70S) composed of identical subunits (30S–35S); 5' structure ($m^7G^5ppp^5NmpNp$); polyadenylated 3' end; repeated sequences at 3' and 5' ends; tRNA base-paired to genome complex |
| Protein | above 60% by weight; gag, internal structural proteins; pol, reverse transcriptase; env, envelope proteins |
| Lipid | about 35% by weight; derived from cell membrane |
| Carbohydrate | about 4% by weight; associated with envelope proteins |
| Physicochemical properties | density 1.16–1.18 g/ml in sucrose, 1.16–1.21 g/ml in cesium chloride; sensitive to lipid solvents, detergents, and heat inactivation (56° C., 30 min); highly resistant to UV- and X-irradiation |
| Morphology | spherical enveloped virions (80–120-nm diameter), variable surface projections (8-nm diameter), icosahedral capsid containing a ribonucleoprotein complex with a core shell (nucleoid) |

In addition, the genome of HIV encodes at least 5 other proteins in addition to those normally found in other retroviruses. These additional genes are designated TAT, ART/TRS, 3'-ORF, SOR and R. HTLV I also contains an additional gene, the pX gene, which may encode up to four proteins (Yarchoan, R. et al., *New England J. Med.* 316: 557–564, 1987; Seiki et al., *Science* 228: 1532–1534, 1985).

All retroviruses have similar overall chemical compositions. In general, they comprise about 60–70% protein, 30–40% lipid, 2–4% carbohydrate, and about 1% RNA. Retroviruses are enveloped. The envelope of retroviral particles is derived from the cell-surface membrane, and most, if not all, of the lipids in the retroviral particles are located in the unit-membrane envelope of the virion. Non-limiting examples of retroviruses include Friend Leukemia Virus (FV), Radiation Leukemia Virus (RadLV), Bovine Leukemia Virus, Feline Leukemia virus, Avian Myeloblastosis Virus, and the human T-cell lymphotropic virus family (HTLV I, II, III and IV; HTLV III is also known as Human Immunodeficiency Virus or HIV in turn encompassing two serotypes designated as HIV-1 and HIV-2). HTLV I is believed to cause adult T-cell leukemia and certain neurological illnesses and HTLV II is believed responsible for hairy cell leukemia in humans. HTLV IV is related to simian immunodeficiency virus and has been found in African natives suffering from AIDS; its relationship to HTLV III is currently under investigation.

The present invention provides a method for treating mammals suffering from infections caused by viruses (or retroviruses) comprising administering to mammals in need of such treatment a therapeutically (or prophylactically) effective amount of a compound selected from the group consisting of PAC compounds and mixtures thereof.

Effective inhibition of a given virus may be achieved by using a single one of such compounds, or a combination of two or more of such compounds. Naturally, it is desirable to employ the smallest possible quantity of the PAC compound or compounds that will provide a significant inhibition of the target virus. What constitutes "significant inhibition" varies from virus to virus. For example, significant inhibition of Fried Leukemia Virus-induced splenomegaly is at least 15% (inhibition being calculated according to the formula given in Example 2, below). Significant inhibition of HIV is defined as at least one log reduction in the infectivity of free virus preparations. In addition, one, two or more of the compounds can be employed together. Moreover, the PAC compounds or mixtures may constitute the sole active ingredient of the composition of the present invention or may be employed in conjunction with other antiviral agents and/or other ingredients active in inhibiting viral replication and/or otherwise diminishing or abolishing viral infectivity (e.g. by inactivating the virus directly).

When treating mammals suffering from infections caused by viruses according to the present invention, the determination of the most effective compound or mixture of compounds for treatment of the particular virus or retrovirus responsible for the infection can be ascertained by routine experimentation using suitable experimental models, such as that described in Example 5 for HIV in vitro or in Example 1 for Friend Leukemia Virus in experimental animals.

When employed in vivo to treat AIDS, viremia (i.e. the presence of virus in the blood stream) or sepsis (viral contamination of bodily fluids) caused by viruses, the PAC compounds may be administered orally, topically or preferably parenterally, and most preferably intravenously at dosages which can be broadly defined by reference to hypericin as follows:

Antiviral compositions containing hypercin as the sole active ingredient can be used at dosages containing from about 0.002 to about 100,000 micrograms per kilogram bodyweight per treatment, preferably between about 2 micrograms and about $5 \times 10^4$ micrograms per kilogram bodyweight per treatment, and most preferably between about 200 micrograms and $5 \times 10^4$ micrograms per kilogram bodyweight per treatment.

When one or more other PAC compounds are used as the active ingredient, the broad dosages will generally be the same as with hypericin. It is understood, however, that if a given PAC compound has e.g. twice the activity of hypericin, the minimum effective dosage will be one-half that of hypericin. Moreover, when more than one active (antiviral) ingredient (i.e., at least one non-PAC antiviral agent is induced) is used in a therapeutic or prophylactic regimen according to the invention, the minimum dosage of the PAC component (i.e., the PAC compound or compounds) of this regimen may be decreased if desired or appropriate. Finally, when more than one active ingredient is used and there is synergism between the PAC component and the other antiviral ingredient or ingredients (or between two or more PAC compounds, even in single active-ingredient regimens, i.e., in regimens where the only antiviral agent or agents are PAC compounds), the minimum effective dosages will be even smaller. It should be also understood that analogous minimum dosage modifications apply when a stabilizing or potentiating agent is used in conjunction with a PAC compound.

To illustrate the foregoing, consider a therapeutic or prophylactic regimen that involves administration of a PAC compound in conjunction with an antivirally active nucleoside analog, as an example of use of more than one active ingredient. (It should be understood that "in conjunction" means coadministered or administered sequentially but as part of the same treatment regimen).

When one or more nucleoside analogs are used in combination with the compounds of the present invention, the nucleoside analog may be administered in conjunction with the PAC compounds) at doses broadly ranging between about 0.001 and about 20,000 micrograms/kg body weight of said mammal per treatment (again based on hypericin). A preferred minimum dose under these circumstances is 1 microgram and a most preferred minimum dose is 100 micrograms all per kg body weight.

The duration and number of doses or treatments required to control the disease will vary from subject to subject, depending upon the severity and stage of the illness and the subject's general condition and will also depend on the specific antiviral activity of each PAC compound, as well as its toxicity (if any). The total dose required for each treatment may be administered in divided doses or in a single dose. The antiviral treatment may be administered daily, more than once daily, one or two times a week, or as determined by the subject's condition and the stage of the disease.

The present inventors have also discovered that the antiviral activity of hypericin is a function of the frequency of treatment. For example, in mouse studies, a single dose of ten micrograms per mouse was less effective than a single dose of 100 micrograms per mouse, as expected. However, administration of 10 micrograms every day for ten days was less effective than even a single 10-microgram dose. By contrast, administration of 10 micrograms once a week was as effective as the single 10-microgram dose. This indicates that the frequency of treatment effects its efficacy. While the foregoing observations in mice may not be applicable to other mammals or humans, those skilled in the art will appreciate that the frequency of treatment is subject to optimization, which can be determined by routine experimentation according to methods well known in the art, e.g. by establishing a matrix of dosage and frequency and assigning a group of experimental subjects to each point of the matrix. Design of this experiment should preferably also take into account the tissue accumulation properties of PAC compounds.

The present invention also provides pharmaceutical compositions and formulations for treating viral infections. The PAC compounds of the present invention can be incorporated in conventional, solid and liquid pharmaceutical formulations (e.g. tablets, capsules, caplets, injectable and orally administrable solutions) for use in treating mammals that are afflicted with viral infections. The pharmaceutical formulations of the invention comprise an effective amount of the PAC compounds of the present invention (as disclosed above) as the active ingredients (alone or in combination with other active or inert agents as discussed above). For example, a parenteral therapeutic composition may comprise a sterile isotonic saline solution containing between about 0.001 micrograms and about 100,000 micrograms of the polycyclic compounds of the present invention and between about 100 and 50,000 micrograms of the nucleoside as described above. It will be appreciated that the unit content of active ingredients contained in an individual dose of each dosage form need not in itself constitute an effective amount since the necessary effective amount can be reached by administration of a plurality of capsules, tablets, injections or combinations thereof.

Each formulation according to the present invention may additionally comprise inert constituents including pharmaceutically-acceptable carriers, diluents, fillers, salts, and other materials well-known in the art the selection of which depends upon the dosage form utilized and the particular purpose to be achieved according to the determination of the ordinarily skilled artisan in the field. For example, tablets may be formulated in accordance with conventional procedures employing solid carriers well known in the art. Examples of solid carriers include, starch, sugar, bentonite, silica and other commonly used carriers. Propylene glycol, benzyl alcohol, isopropanol, ethanol, dimethylsulfoxide (DMSO) dimethylacetamide or other biologically acceptable organic solvents or aqueous solutions (e.g. water with a pH higher than 7 and preferably about 8) may be used as diluents, carriers or solvents in the preparation of solid and liquid pharmaceutical formulations containing the anti-retroviral compositions of the present invention. Further nonlimiting examples of carriers and diluents include carbohydrates, albumin and/or other plasma protein components such as low density lipoproteins, high density lipoproteins and the lipids with which these serum proteins are associated. Such lipids include phosphatidyl choline, phosphatidyl serine, phosphatidyl ethanolamine and neutral lipids such as triglycerides. Additional lipid carriers include without limitation tocopherol, retinoic acid and cyclodextranes. Semisolid formulations such as those well-known in the art (e.g. suppositories) are also contemplated.

Preferred parenteral dosage forms may comprise for example an isotonic saline solution, containing between about 0.1 micrograms and about 100,000 micrograms of the polycyclic compounds of the present invention.

Capsules employed in the present invention may be made from any pharmaceutically acceptable material, such as gelatin or cellulose derivatives. Sustained release oral and transdermal delivery systems are also contemplated.

The antiviral polycyclic compounds of the present invention may additionally be incorporated into liposomes for use as specific drug carriers. Such liposomes may also comprise other active agents e.g., specific anti-HIV antibodies directed against viral proteins expressed by virally infected cells such as HIV p120, p41 and p24 (as well as glycosylated forms thereof) to act as specific targeting agents.

The present invention is described below and specific working examples which are intended to illustrate the invention without limiting the scope thereof.

EXAMPLE 1

Anti-Retroviral Effect of the Polycyclic Compounds of the Present Invention (a) Effects of PAC Compounds Used Alone.

The effects of compositions according to the present invention on infection of mammals with Friend Leukemia Virus (FV) were examined.

Friend Leukemia Virus is an aggressive retrovirus which induces an acute erythroleukemia in sensitive strains of mice such as BALB/c and NIH swiss mice as described in Friend, C. J., *Exp. Med.* 105: 307–324, 1957; Friend, C. et al. *Proc. Natl. Acad. Sci. USA* 68: 378–383, 1971; Friend, C. et al. *Natl. Cancer Inst. Mongr.* 22: 508–552, 1966. The malignant transformation is the result of the combined activities of the Spleen Focus Forming Virus (SFFV) and the ecotropic Murine Friend Leukemia Helper Virus (F-MuLV). The acute erythroleukemia is characterized by hepatosplenomegaly (a marked increase in the size of the spleen and liver) and a severe anemia.

Friend Leukemia Virus was prepared by homogenizing the enlarged spleen of a mouse previously infected with FV, 10 days after intravenous virus injection. The spleen was homogenized in phosphate buffered saline in a volume equal to ten times the weight of the isolated spleen.

The effects of compositions according to the present invention on the increase in spleen size (splenomegaly) of BALB/c mice (Jackson Labs, Bar Harbor, ME) was examined. In these experiments, the virus ($10^6$ focus forming units—FFU) was inoculated intravenously and 100 micrograms of the compounds indicated in Table II were administered to the mice intraperitoneally 24 hours later. Each compound was administered once to two mice. The animals were sacrificed ten days later and their spleens weighed. Each compound listed below in Table II had five or more fused aromatic rings in any configuration and hence constitutes an analog of a Formula I compound.

While the Friend virus system permits testing the activity of the compounds of the present invention, in an acute infection system several points should be noted. Transformation of erythroid precursor cells occurs rapidly after virus inoculation. Once transformation by FV occurs, disease is likely to result. Therefore., any inhibition of viral splenomegaly caused by FV by the compounds of the present invention indicates a strong effectiveness for a rapidly-evolving disease and therefore the active compounds of the present invention will also be effective against a slowly-evolving disease. Hence, the results presented above may be extrapolated to a slower and gradually progressive disease such as that caused by HIV.

The present assay has been developed from similar assays using hypericin or pseudohypericin and employing higher numbers of experimental animals per group (e.g. 4 animals). It was discovered however that the specificity and sensitivity of this assay are such that an experimental group of two animals is of more than adequate predictive value.

The results are shown in Table II below.

TABLE II

| Treatment | Actual Spleen Weight | Average Spleen Weight | Average % Inhibition |
|---|---|---|---|
| PBS (negative control) | 0.1560 | 0.1495 | — |
|  | 0.1429 |  |  |
| FV (positive control) | 0.8316 | 0.8550 | — |
|  | 0.8799 |  |  |
| 1. Decacyclene | 0.3940 | 0.3636 | 57.5 |
|  | 0.3331 |  |  |
| 2. 3,4,9,10-Perylenetetracarboxylic dianhydride | 0.8678 | 0.8439 | 1.3 |
|  | 0.8200 |  |  |
| 3. Isoviolanthrone | 0.5147 | 0.5001 | 41.5 |
|  | 0.4855 |  |  |
| 4. 16,17-Dihydroxydibenzanthrone | 0.4151 | 0.4194 | 50.9 |
|  | 0.4234 |  |  |
| 5. Benzo(GHI)Perylene-1,2-Dicarboxylic Anhydride | 0.5072 | 0.5101 | 40.5 |
|  | 0.5130 |  |  |
| 6. 3,4-Coronenedicarboxylic anhydride | 0.8704 | 0.8700 | — |
|  | 0.8695 |  |  |
| 7. Triptycene | 0.4578 | 0.4655 | 45.6 |
|  | 0.4732 |  |  |
| 8. Coronene 97% | 0.4682 | 0.4739 | 44.6 |
|  | 0.4796 |  |  |
| 9. 3-Bromophenanthro(3,4-C)Phenanthrene | 0.8875 | 0.8756 | — |
|  | 0.8637 |  |  |
| 10. Diindeno(1,2,3-CD/1',2',3'-IM)Perylene | 0.4809 | 0.4767 | 44.3 |
|  | 0.4724 |  |  |
| 11. 3-Methylphenanthro(3,4-C)Phenanthrene | 0.4308 | 0.4235 | 50.5 |
|  | 0.4162 |  |  |
| 12. 4A,5,6,12C-Tetrahydro-3-Methylphenanthro (3,4-C)phenanthrene | 0.4400 | 0.4531 | 47.1 |
|  | 0.4661 |  |  |
| 13. 3,4,4A,5,6,12C-Hexahydrophenanthro (3,4-C)Phenanthrene-3,6-Dione | 0.4719 | 0.4742 | 44.6 |
|  | 0.4765 |  |  |
| 14. Phenanthro(3,4-C)Phenanthrene | 0.5580 | 0.5419 | 36.6 |
|  | 0.5257 |  |  |
| 15. 3,4,4A,5,6,12C-Hexahydrophenanthro (3,4-C)phenanthren-3-one | 0.3802 | 0.3739 | 56.3 |
|  | 0.3677 |  |  |

As can be seen in Table II, PAC compounds 1, 3–5, 7, 8 and 10–15 significantly inhibited FV-induced splenomegaly. As used in Table II (and subsequent Tables of this Example 1(a) and (b), "average percent inhibition" is calculated as follows:

$$\left(1 - \frac{ASWE - ASWNC}{ASWPC - ASWNC}\right) \times 100$$

wherein "ASWNC" designates "average spleen weight of negative control"; "ASWE" designates "average spleen weight of experimental (treated) subject"; and "ASWPC" designates "average spleen weight of positive control". Average spleen weight is the numerical average of spleen weights of each experimental group (in Table II each such group includes two members).

The results of a similar experiment using hypericin and pseudohypericin described in U.S. ppplication Ser. No. 84,008 are set forth below.

In these experiments, the virus ($10^6$ focus forming units—FFU) was inoculated intravenously, and the indicated doses of the antiviral compounds of this invention were administered to the BALB/c mice intraperitoneally 24 hours later. The animals were then sacrificed ten days later and their spleens weighed. The results are summarized in Table II(a) below.

Pseudohypericin was diluted in phosphate buffered saline with 1% ethanol.

TABLE II(a)

| Negative Control Mice (PBS) | Positive Control (FV inoculated) Mice ($10^6$ FFU) |
|---|---|
| 0.2094 Spleen weight (gms) | 1.0272 Spleen weight (gms) |
| 0.1834 Spleen weight (gms) | 0.9596 Spleen weight (gms) |
| 0.1790 Spleen weight (gms) | 1.2432 Spleen weight (gms) |
| 0.1669 Spleen weight (gms) | 1.1174 Spleen weight (gms) |
| x = 0.1846 ± 0.0178 | x = 1.0865 ± 0.1226 |
|  | Net change from control = 0.9019 |
| Friend Virus ($10^6$ FFU) + PS 80 mcg/mouse | Friend Virus ($10^6$ FFU) + 2 injections PS 80 mcg/mouse |
| 0.2831 Spleen weight (gms) | 0.2457 Spleen weight (gms) |
| 0.2761 Spleen weight (gms) | 0.3400 Spleen weight (gms) |
| 0.2215 Spleen weight (gms) | 0.2938 Spleen weight (gms) |
| 0.1810 Spleen weight (gms) | 0.1956 Spleen weight (gms) |
| x = 0.2404 ± 0.0482 | x = 0.2687 ± 0.0621 |
| Net change from control = 0.0558 | Net change from control = 0.0841 |
| % Inhib = 93.82 | % Inhib = 90.70 |
| Negative Control Mice (PBS) | Positive Control (Friend) Mice ($2 \times 10^5$ FFU) |
| 0.2094 Spleen weight (gms) | 0.8911 Spleen weight (gms) |
| 0.1834 Spleen weight (gms) | 0.9211 Spleen weight (gms) |
| 0.1790 Spleen weight (gms) | 0.8004 Spleen weight (gms) |
| 0.1669 Spleen weight (gms) | 0.8662 Spleen weight (gms) |
| x = 0.1846 ± 0.0178 | x = 0.8697 ± 0.0513 |
|  | Net change from control = 0.6851 |

TABLE II(a)-continued

| Friend Virus (2 × 10⁵ FFU) + PS 80 mcg/mouse | Friend Virus (2 × 10⁵ FFU) 2 inject PS 80 mcg/mouse |
|---|---|
| 0.3457 Spleen weight (gms) | 0.4924 Spleen weight (gms) |
| 0.2784 Spleen weight (gms) | 0.2469 Spleen weight (gms) |
| 0.2208 Spleen weight (gms) | 0.2722 Spleen weight (gms) |
| 0.1791 Spleen weight (gms) | 0.2438 Spleen weight (gms) |
| x = 0.2560 ± 0.0723 | x = 0.3138 ± 0.1197 |
| Net change from control = 0.0714 | Net change from control = 0.1292 |
| % Inhib = 89.58 | % Inhib = 81.15 |

The data in Table II(a) show the inhibition of splenomegaly, with median inhibition of 93.8%, following a single injection of 80 micrograms per mouse of Ps. A median inhibition of 89.6% in spleen enlargement was observed when 80 micrograms per mouse of Ps was administered in a single injection to mice that had previously been inoculated with 0.5 ml of the virus preparation (corresponding to 2×10⁵ FFU of virus). When two daily consecutive injections of Ps, each comprising 80 micrograms per mouse of the compound were administered, the median inhibition of splenomegaly was 90.7% with a viral preparation containing 10⁶ FFU and 81.7% with a viral preparation containing 2×10⁵ FFU (Table 1).

The above results show a marked decrease in the spleen enlargement capacity of the Friend Leukemia Virus (as measured by decreased splenomegaly) following the intraperitoneally administration of Ps 24 hours after infection.

The same type of experiment can be used to measure the antiviral activity of other PAC compounds.

(2) Co-administration with Friend Leukemia Virus

A different experimental design was used involving the simultaneous intravenous co-administration of Ps with the FV complex. In this case, the viral preparation was mixed with Ps at various concentrations and the mixture was injected into the mouse tail vein in a final volume of 0.5 ml. The mice were sacrificed ten days later, their spleens weighed, and the level of inhibition of splenomegaly subsequently determined. The results are summarized in Table II(b).

TABLE II(b)

The effect of intravenous co-administration of pseudohypericin (diluted in PBS with 1% EtOH) with FV, on viral-induced splenomegaly.

As shown in Table II(b) above, 100% inhibition of splenomegaly was found when Ps was administered with the viral complex at concentrations of 20 micrograms per mouse and 50 micrograms per mouse (average mouse weight approximately 150 grams). A mean inhibition of 75.44% was found when 5 micrograms per mouse was co-administered with the virus.

These results show the effectiveness of the compounds of the present invention in that as little as 5 micrograms per mouse was effective in inhibiting viral transformation by this aggressive RNA tumor virus.

An expanded series of experiments was next performed in which various concentrations (i.e. 50, 100, 200 and 2×100, i.e., 100 micrograms administered twice) of a different set of PAC compounds (numbers 16–29 and 30–36 in Table III below) were administered intraperitoneally each according to the same protocol described above. Compounds 16–29 all had 3–5 fused, aromatic rings and no side groups except for oxygen or hydroxyl groups, whereas compounds 30–36 all had 3 fused aromatic rings and side chains selected from the group of oxygen, hydroxyl and methyl.

When 2 doses of the compounds were given, the second dose was administered 24–48 hours after the first injection. The animals were infected and splenomegaly determined as above for the compounds in Table II. The results are presented in Table III below. In Table III, "pooled average percent inhibition" is calculated by adding the average percent inhibition for each experiment with the same compound and dividing the sum by the number of experiments (i.e. the number 4).

The standard deviation was computed by pooling all the data for each compound (i.e. all concentrations of a compound employed) and therefore the large standard deviation values given reflect only the variablility of the data over the range of concentrations used for each compound. As can be seen from the spleen weight values, the PAC compounds in Table III have a definite inhibitory effect.

| | Controls | | Spleen Weights (grams) | | |
| | | | Expt1 | Expt2 | Expt3 |
|---|---|---|---|---|---|
| PBS | PBS + 1% EtOH | FV | FV + PS 5 mcg | FV + PS 20 mcg | FV + PS 50 mcg |
| 0.1304 | 0.1862 | 1.1499 | 0.3425 | 0.1655 | 0.1830 |
| 0.1490 | 0.1567 | 1.0657 | 0.3766 | 0.1426 | 0.1674 |
| 0.1362 | 0.1386 | 0.9597 | 0.4005 | 0.1433 | 0.1422 |
| 0.1515 | | 1.1347 | 0.4255 | 0.1966 | 0.1365 |
| x = 0.1417 ± | x = 0.1605 ± | x = 1.0774 ± | x = 0.3862 ± | x = 0.1614 ± | x = 0.1572 ± |
| 0.0101 | 0.0240 | 0.0866 | 0.0353 | 0.0253 | 0.0217 |
| % inhibition as compared to the group receiving Ps in PBS + 1% EtOH | | = | 75.44% | 100% | 100% |

TABLE III

| Treatment | Dose | Actual Spleen Weight | Average Spleen Weight | Perdosage Average % Inhibition | Pooled Average % Inhibition | Standard Deviation |
|---|---|---|---|---|---|---|
| FIRST SET OF EXPERIMENTS | | | | | | |
| PBS (negative control) | | 0.1247 | | | | |
| | | 0.142 | 0.1334 | | | |
| | | 1.4626 | | | | |
| FV (positive control) | | 1.7272 | 1.5949 | | | |
| | | 0.9062 | | | | |
| 16. Dodecahydrotriphenylene | 50 | 0.9954 | 0.9508 | 44 | 24 | 16 |
| | | 1.6206 | | | | |
| | 100 | 1.5907 | 1.6057 | — | | |
| | | 1.2007 | | | | |
| | 200 | 1.2948 | 1.2478 | 24 | | |
| | | 1.161 | | | | |
| | 2 × 100 | 1.2072 | 1.1867 | 28 | | |
| | | 1.06 | | | | |
| 17. Phenanthrene | 50 | 1.21 | 1.1350 | 31 | 26 | 8 |
| | | 1.3626 | | | | |
| | 100 | 1.2101 | 1.2864 | 21 | | |
| | | 1.4602 | | | | |
| | 200 | 1.24 | 1.3501 | 17 | | |
| | | 1.0704 | | | | |
| | 2 × 100 | 1.0662 | 1.0683 | 36 | | |
| | | 1.1141 | | | | |
| 18. Phenylanthracene | 50 | 1.2464 | 1.1803 | 28 | 19 | 10 |
| | | 1.6206 | | | | |
| | 100 | 1.4902 | 1.554 | 3 | | |
| | | 1.3797 | | | | |
| | 200 | 1.2794 | 1.3296 | 18 | | |
| | | 1.4116 | | | | |
| | 2 × 100 | 1.0222 | 1.2169 | 26 | | |
| | | 1.0961 | | | | |
| 19. Triphenylene | 50 | 1.0036 | 1.0499 | 37 | 17 | 12 |
| | | 1.5971 | | | | |
| | 100 | 1.4719 | 1.5345 | 4 | | |
| | | 1.3636 | | | | |
| | 200 | 1.4352 | 1.3994 | 13 | | |
| | | 1.246 | | | | |
| | 2 × 100 | 1.5665 | 1.4063 | 13 | | |
| | | 1.3209 | | | | |
| 20. Dihydrophenanthrene | 50 | 1.2307 | 1.2758 | 22 | 3 | 19 |
| | | 2.0411 | | | | |
| | 100 | 1.9626 | 2.0019 | — | | |
| | | 1.4003 | | | | |
| | 200 | 1.4626 | 1.4315 | 11 | | |
| | | 1.4929 | | | | |
| | 2 × 100 | 1.5117 | 1.5023 | 6 | | |
| | | 1.4102 | | | | |
| 21. 1,4,5,8,9,10-Hexahydroanthracene | 50 | 1.3969 | 1.4036 | 13 | 17 | 4 |
| | | 1.4907 | | | | |
| | 100 | 1.3334 | 1.4121 | 13 | | |
| | | 1.4772 | | | | |
| | 200 | 1.1121 | 1.2947 | 21 | | |
| | | 1.3242 | | | | |
| | 2 × 100 | 1.2006 | 1.2624 | 23 | | |
| | | 0.9242 | | | | |
| 22. 9,10-Diphenylanthracene | 50 | 1.063 | 0.9936 | 41 | 15 | 16 |
| | | 1.4116 | | | | |
| | 100 | 1.6226 | 1.5171 | 5 | | |
| | | 1.5997 | | | | |
| | 200 | 1.5828 | 1.5913 | 0 | | |
| | | 1.4611 | | | | |
| | 2 × 100 | 1.3629 | 1.4120 | 13 | | |
| | | 1.1961 | | | | |
| 23. 1,2,3,6,7,8-Hexahydropyrene | 50 | 1.2222 | 1.2092 | 26 | 25 | 11 |
| | | 1.6114 | | | | |
| | 100 | 1.4147 | 1.5131 | 6 | | |
| | | 1.0303 | | | | |
| | 200 | 1.1618 | 1.0961 | 34 | | |
| | | 1.0119 | | | | |
| | 2 × 100 | 1.2443 | 1.1281 | 32 | | |
| | | 1.3016 | | | | |
| 24. Tetraphenylcyclo pentadienone | 50 | 1.2902 | 1.2959 | 20 | 16 | 7 |
| | | 1.3774 | | | | |
| | 100 | 1.4106 | 1.3940 | 14 | | |
| | | 1.61 | | | | |

TABLE III-continued

| Treatment | Dose | Actual Spleen Weight | Average Spleen Weight | Perdosage Average % Inhibition | Pooled Average % Inhibition | Standard Deviation |
|---|---|---|---|---|---|---|
| | 200 | 1.404 | 1.5070 | 6 | | |
| | | 1.2876 | | | | |
| | 2 × 100 | 1.1998 | 1.2437 | 24 | | |
| | | 1.2062 | | | | |
| 25. 2-Methylanthracene | 50 | 1.2146 | 1.2104 | 26 | 30 | 4 |
| | | 1.0062 | | | | |
| | 100 | 1.1149 | 1.0606 | 37 | | |
| | | 1.2106 | | | | |
| | 200 | 1.1702 | 1.1904 | 28 | | |
| | | 1.19 | | | | |
| | 2 × 100 | 1.1616 | 1.1758 | 29 | | |
| | | 1.2003 | | | | |
| 26. 1,2,3,4-Tetraphenyl-1,3-cyclopentadiene | 50 | 1.1967 | 1.1985 | 27 | 25 | 15 |
| | | 0.9898 | | | | |
| | 100 | 1.0662 | 1.0280 | 39 | | |
| | | 1.0779 | | | | |
| | 200 | 1.1482 | 1.1131 | 33 | | |
| | | 1.2161 | | | | |
| | 2 × 100 | 1.977 | 1.5966 | 0 | | |
| | | 1.2226 | | | | |
| 27. Perylene | 50 | 1.407 | 1.3148 | 19 | 9 | 7 |
| | | 1.5572 | | | | |
| | 100 | 1.4982 | 1.5227 | 5 | | |
| | | 1.5066 | | | | |
| | 200 | 1.7022 | 1.6044 | 1 | | |
| | | 1.496 | | | | |
| | 2 × 100 | 1.3723 | 1.4342 | 11 | | |
| | | 1.2351 | | | | |
| 28. Pentacene | 50 | 1.3209 | 1.2780 | 22 | 12 | 6 |
| | | 1.4996 | | | | |
| | 100 | 1.5772 | 1.5384 | 4 | | |
| | | 1.4806 | | | | |
| | 200 | 1.3749 | 1.4278 | 11 | | |
| | | 1.4208 | | | | |
| | 2 × 100 | 1.3996 | 1.4102 | 13 | | |
| | | 1.6182 | | | | |
| 29. 9-Vinylanthracene | 50 | 1.6851 | 1.6517 | 4 | 14 | 11 |
| | | 1.1792 | | | | |
| | 100 | 1.2606 | 1.2199 | 26 | | |
| | | 1.2933 | | | | |
| | 200 | 1.2933 | 1.2933 | 21 | | |
| | | 1.3747 | | | | |
| | 2 × 100 | 1.3747 | 1.3747 | 15 | | |
| SECOND SET OF EXPERIMENTS | | | | | | |
| PBS (negative control) | — | 0.2061 | | | | |
| | | 0.1551 | 0.1806 | — | | |
| FV (positive control) | — | 2.0462 | | | | |
| | | 2.1004 | 2.0733 | — | | |
| Hy (hypericin) | 150 mg | 0.7245 | | | | |
| | | 0.8169 | 0.7707 | 63 | | |
| 30. Anthrone | 50 | 1.4837 | 1.4953 | 31 | 53 | 13 |
| | | 1.5069 | | | | |
| | 100 | 0.8623 | 0.8790 | 63 | | |
| | | 0.8957 | | | | |
| | 200 | 0.9567 | 0.9092 | 62 | | |
| | | 0.8616 | | | | |
| | 2 × 100 | 0.9799 | 0.9878 | 57 | | |
| | | 0.9956 | | | | |
| 31. Xanthone | 50 | 0.965 | 1.0006 | 57 | 59 | 2 |
| | | 1.0362 | | | | |
| | 100 | 0.9708 | 0.9806 | 58 | | |
| | | 0.9903 | | | | |
| | 200 | 0.9866 | 0.9431 | 60 | | |
| | | 0.8996 | | | | |
| | 2 × 100 | 0.8744 | 0.9003 | 62 | | |
| | | 0.9262 | | | | |
| 32. Anthraflavic acid | 50 | 1.7072 | 1.5718 | 26 | 50 | 15 |
| | | 1.4363 | | | | |
| | 100 | 1.1367 | 1.1542 | 49 | | |
| | | 1.1717 | | | | |
| | 200 | 0.8236 | 0.8593 | 64 | | |
| | | 0.8949 | | | | |
| | 2 × 100 | 0.961 | 0.9325 | 60 | | |
| | | 0.904 | | | | |

TABLE III-continued

| Treatment | Dose | Actual Spleen Weight | Average Spleen Weight | Perdosage Average % Inhibition | Pooled Average % Inhibition | Standard Deviation |
|---|---|---|---|---|---|---|
| 33. 2-phenyl-1,2 inadione | 50 | 0.9376 0.9444 | 0.9410 | 60 | 51 | 21 |
| | 100 | 1.8237 1.7288 | 1.7763 | 16 | | |
| | 200 | 0.7737 0.8138 | 0.7938 | 68 | | |
| | 2 × 100 | 0.9522 0.8732 | 0.9127 | 61 | | |
| 34. Emodin 99% | 50 | 1.3341 1.2487 | 1.2914 | 41 | 38 | 11 |
| | 100 | 1.1661 1.1005 | 1.1333 | 50 | | |
| | 200 | 1.7441 1.6363 | 1.6902 | 20 | | |
| | 2 × 100 | 1.2635 1.3033 | 1.2834 | 42 | | |
| 35. 2-(hydroxymethyl)-anthraquinone | 50 | 0.8845 0.8996 | 0.8921 | 62 | 70 | 7 |
| | 100 | 0.934 0.7889 | 0.8615 | 64 | | |
| | 200 | 0.5399 0.6772 | 0.6086 | 77 | | |
| | 2 × 100 | 0.6006 0.7144 | 0.6575 | 75 | | |
| 36. Bianthrone | 50 | 1.1042 1.0636 | 1.0839 | 52 | 52 | 3 |
| | 100 | 1.1443 1.1707 | 1.1575 | 48 | | |
| | 200 | 1.0063 0.9877 | 0.9970 | 57 | | |
| | 2 × 100 | 1.0606 1.21 | 1.1353 | 50 | | |

As can be seen from the results in Table III compounds 30–36 (having 3 fused aromatic rings and side groups of methyl, oxygen or hydroxyl) were generally more effective than compounds 16–29 (having 3–5 fused aromatic rings and no side groups). It should be noted that all of the compounds tested in the experiments described in this Example showed at least some degree of anti-retroviral activity. The same experiment can be used to measure the antiviral activity of other PAC compounds.

All compounds used in this Example l(a) can be obtained from Aldrich Chemical Co., Milwaukee, Wis., and are referred to herein as Series B compounds. Their structural formulas are set forth in Example 2, below.

(b) Effects of Polycyclic Compounds In Combination With Nucleoside Analogs

The compounds of the present invention (100 micrograms per mouse) were also tested in combination with AZT (20 micrograms per mouse, twice a day) using otherwise the same methods as in Example 1(a) above. As representatives, compound #9 above (3-bromophenanthro (3,4-C), phenanthrene) and compound #10 (diindeno (1, 2, 3-CD/1', 2', 3'-IM) Perylene) were chosen. As shown in Table II above, compound #9 had shown weak anti-retroviral activity when administered at 100 micrograms per mouse whereas compound #10 showed significant (>40%) inhibition of FV-induced splenomegaly. The compounds were administered i.p. either once or five times (once per day) alone or together with AZT (20 micrograms of AZT per mouse twice a day for five days?). Thus, in experiments where AZT was administered five times, a total of 100 micrograms of AZT was received by each mouse (with a total of 500 micrograms of the PAC compound). The results are shown in Table IV below.

TABLE IV

| Treatment | Spleen weight | Average | % Inhibition |
|---|---|---|---|
| PBS | 0.1637 0.159 | 0.16135 | — |
| FV | 2.2297 2.0875 | 2.1586 | — |
| 1X #9 | 2.0831 2.1317 | 2.1074 | 3 |
| 5X #9 | 1.6262 1.7363 | 1.68125 | 24 |
| 1X #10 | 1.7816 1.6664 | 1.724 | 22 |
| 5X #10 | 1.5771 0.8945 | 1.2358 | 46 |
| 5X AZT (20 micrograms per mouse) | 1.3744 1.4046 | 1.3895 | 39 |
| 5X (AZT + #9) (20 micrograms + 100 micrograms of #9 per mouse) | 0.9097 0.9619 | 0.9358 | 61 |
| 5X (AZT + #10) (20 micrograms + 100 micrograms of #10 per mouse) | 0.9787 1.0611 | 1.0199 | 57 |

As shown in Table IV above, although compound #9 showed weak anti-retroviral activity when administered once (3%) or five times over a period of five days (24%). When the same compound was co-administered with AZT, substantial inhibition of FV-induced splenomegaly (61%) was found. This increase in inhibitory activity is not attributable to AZT alone, since the same amount of AZT alone caused only 39% inhibition. Hence, the co-administration of the present compounds and AZT constitutes a regimen of at least additive effectiveness compared to the administration of either active ingredient alone.

Administration of compound #10 (which demonstrated significant anti-retroviral activity when administered alone) in conjunction with AZT not only led to substantial retroviral inhibition (57%) but this inhibition was also greater than the inhibition found when each drug was administered alone.

Based on the above tests involving PAC compounds and/or tests of hypericin and pseudohypericin combined with AZT, it is anticipated that other PAC compounds will have at least additive activity when used therapeutically or preventively in conjunction with AZT or another nucleoside analog.

Therefore, the above data in Table IV show the enhanced efficacy of the PAC compounds when combined with nucleoside analogs such as AZT when treating a retroviral infection. The results of a similar experiment using hypericin and pseudohypericin together with AZT show that hypericin-containing compositions and also containing AZT have antiviral activity (and splenomegaly-inhibitory activity) that is higher than the activity of either the PAC compound or the nucleoside.

EXAMPLE 2

Listed below are a series of PAC compounds (Series A). Due to their structural similarity with hypericin, they are expected to be active against viruses and retroviruses. These compounds are available upon request from the National Cancer Institute, Bethesda, Md. and their properties have been described in Weiss, U. et al. *Progress in Chemistry of Organic Natural Products* 52:1–71, 1987.

A1. CAS Registry No. 14343921
A2. CAS Registry No. 6336841
A3. CAS Registry No. 14642729
A4. CAS Registry No. 6336874
A5. CAS Registry No. 6941475
A6. CAS Registry No. 4478766
A7. CAS Registry No. 2013583
A8. CAS Registry No. 667914
A9. CAS Registry No. 434855
A10. CAS Registry No. 3438082
A11. CAS Registry No. 24541193
A12. CAS Registry No. 10395025
A13. [NSC No. 123399-N]

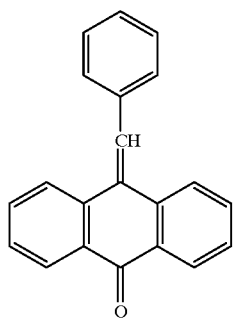

A14. CAS Registry No. 69544850
A15. CAS Registry No. 55043419
A16. CAS Registry No. 71205384
A17. CAS Registry No. 52236541
A18. [NSC No. 231579-Y]

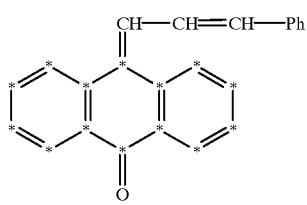

A19. [NSC No. 241039-I]

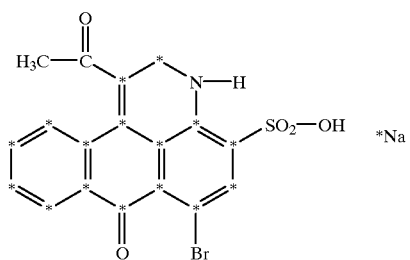

A20. CAS Registry No. 27575468
A21. [NSC No. 308787-V]

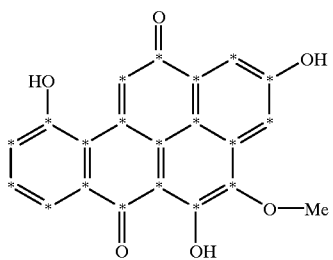

A22. [NSC No. 308805-Q]

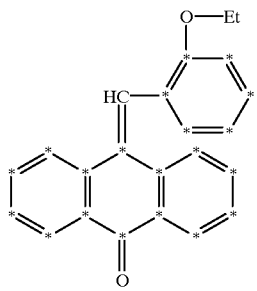

A23. [NSC No. 308814-Z]

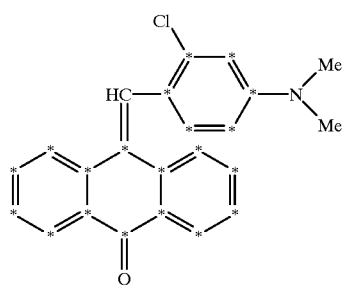

Series B

1.

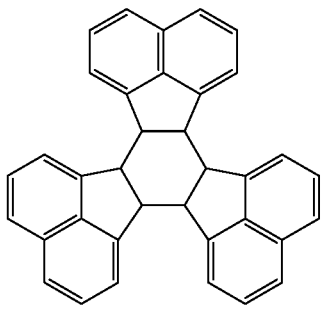

A24. CAS Registry No. 14343954

A25. Rondomycin, 2-Naphthacenecarboxamide, NSC No. 356465-U

2.

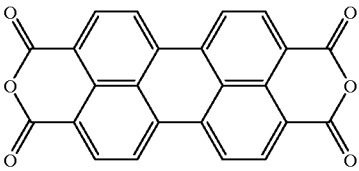

3.

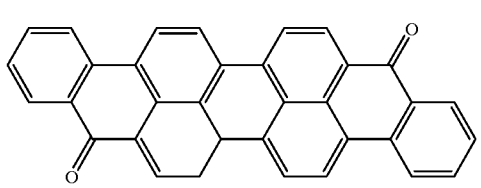

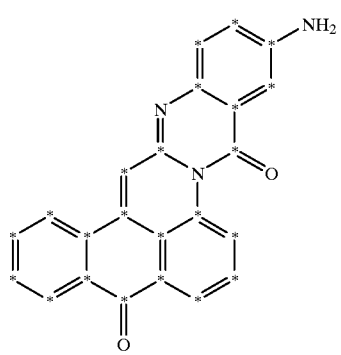

A26. CAS Registry No. 81092844
A27. CAS Registry No. 81092855
A28. [NSC No. 507458-S]

4.

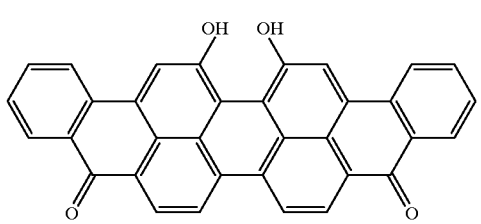

5.

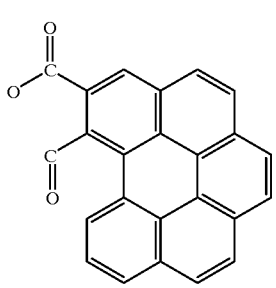

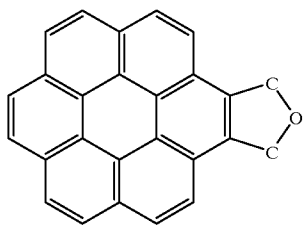

6.

Listed below are a series of compounds (Series B) which are PAC compounds (including AAB compounds and analogs or derivatives of AAB compounds). Due to their structural similarity with hypericin, they are expected to be active against viruses and retroviruses. These compounds are available from Aldrich Chemical Co. The names of these compounds are in Tables II and III of Example 1.

7. 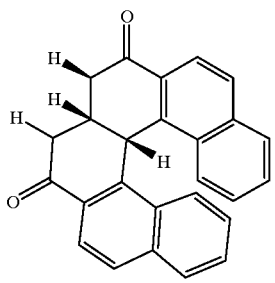
8. 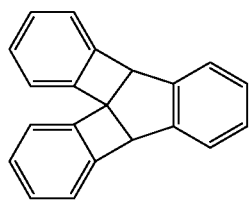
9. 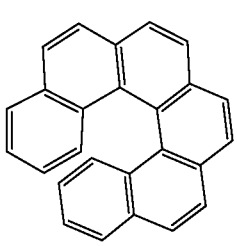
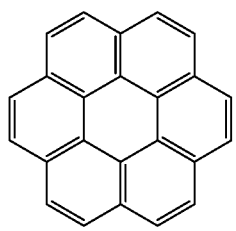
10. 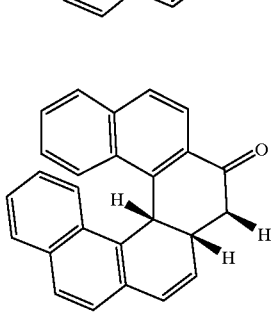
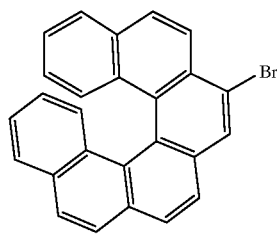
11. 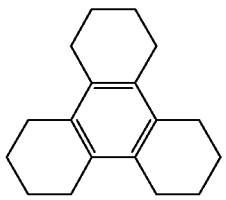
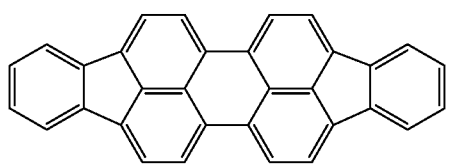
12. 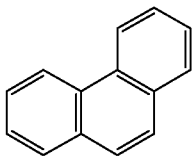
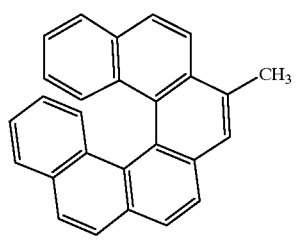
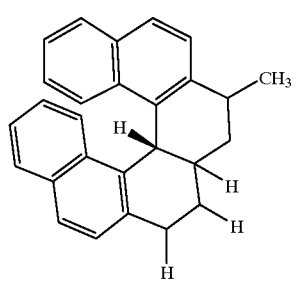
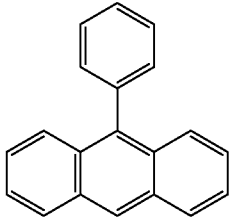

-continued
19.
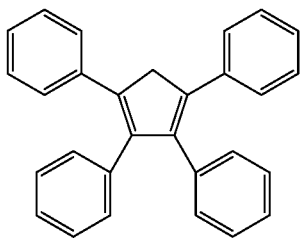
20.
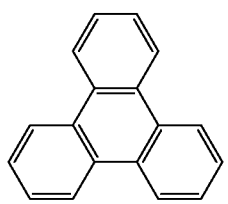
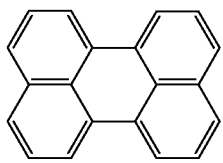
21.
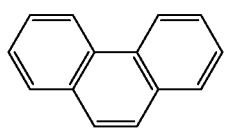
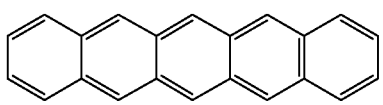
22.
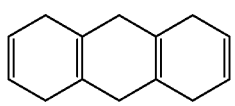
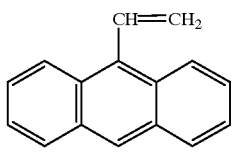
23.
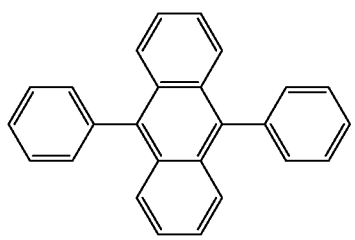
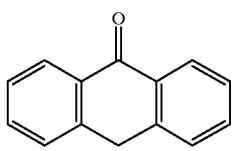
24.
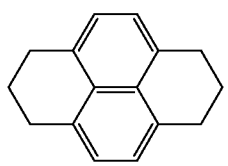
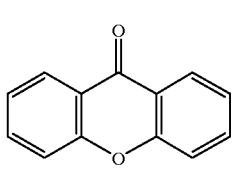
25.
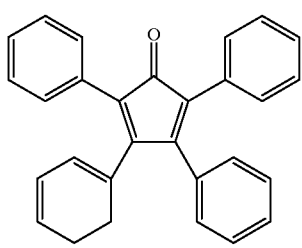
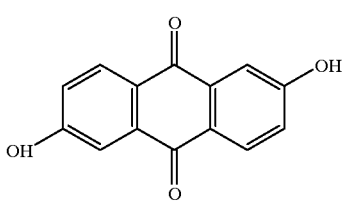
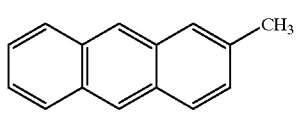

34.
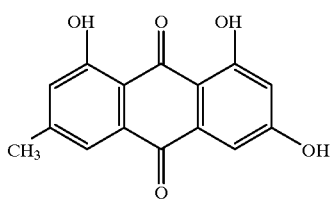
35.
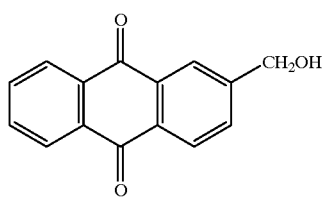
36.
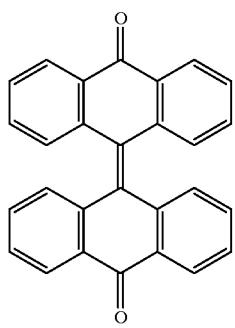
The properties of the following AAB compounds, 1–25 (Series C) have been described in Banks, H. J. et al., *Aust. J. Chem.* 29: 1509–1521, 1976.
Series C
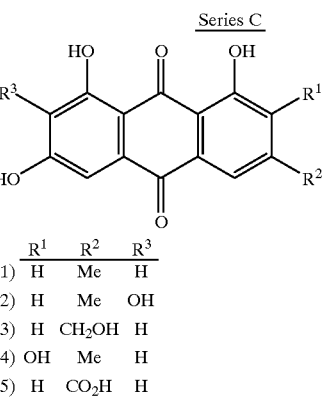
|     | $R^1$ | $R^2$ | $R^3$ |
|-----|-------|-------|-------|
| (1) | H | Me | H |
| (2) | H | Me | OH |
| (3) | H | $CH_2OH$ | H |
| (4) | OH | Me | H |
| (5) | H | $CO_2H$ | H |
(6)
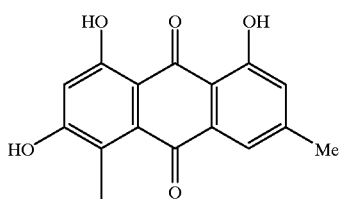
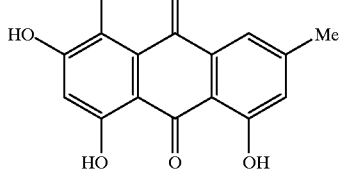
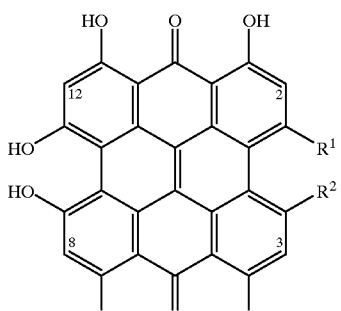
| | $R^1$ | $R^2$ |
|---|---|---|
| (7) | Me | Me |
| (8) | Me | $CO_2H$ |
| (9) | $CO_2H$ | $CO_2H$ |
| (10) | Me | $CH_2OH$ |
(11)
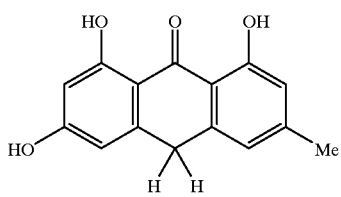
(12)
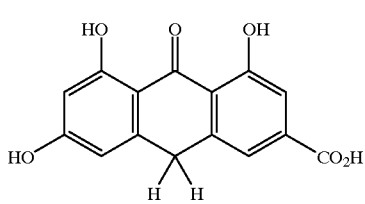

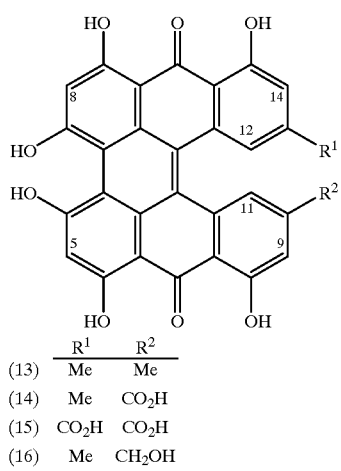

(13) R¹ = Me, R² = Me
(14) R¹ = Me, R² = CO₂H
(15) R¹ = CO₂H, R² = CO₂H
(16) R¹ = Me, R² = CH₂OH

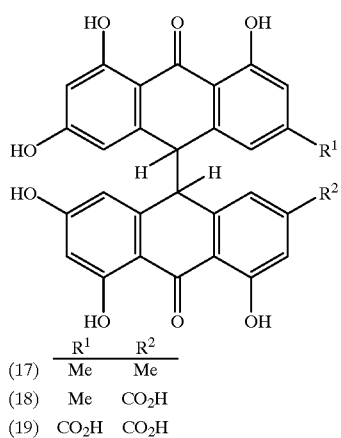

(17) R¹ = Me, R² = Me
(18) R¹ = Me, R² = CO₂H
(19) R¹ = CO₂H, R² = CO₂H (20)

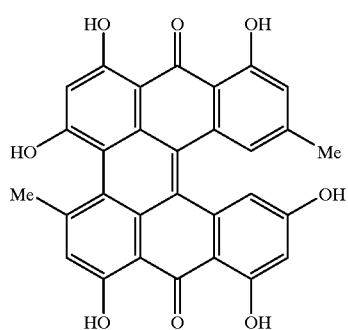

(21)

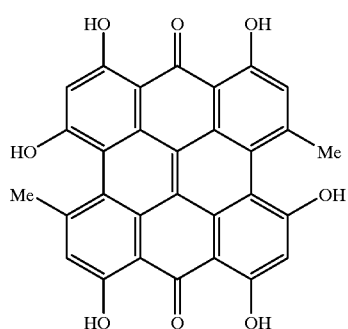

(22)

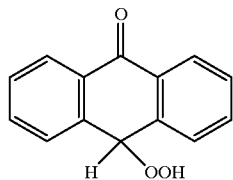

(23)

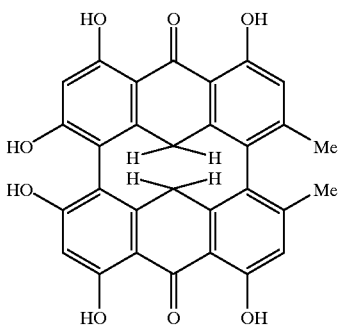

(24)

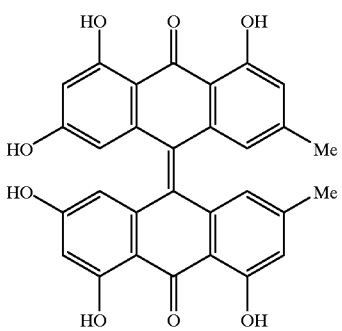

(25)

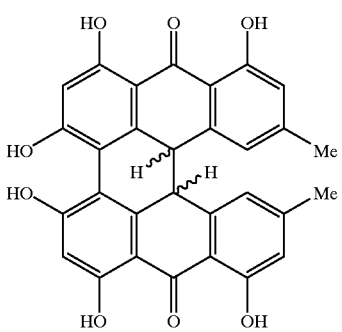

The synthesis and/or isolation of compounds 1–25 (Series C) listed above are specifically described in the following references:

1. Emodin. Commercially available from Aldrich. Synthesis from 3,5 dimethoxy-o-phthalic anhydride and m-cresol U.S. Pat. No. 2,707,704 of Brockmann et al, also from Ahmed, S. A. et al *J. Chem. Soc. Chem. Commun.* 1987, pp. 883–884 which also discloses synthesis for various hydroxyemodins.
2. 7-hydroxyemodin. Banks, H. J. et al., *Aust. J. Chem.*, 29:1509–1521, 1976.
3. Omega-hydroxyemodin. Banks, supra.
4. alaternin (2-hydroxyemodin). Banks, supra.
5. Emodic Acid. Synthesis from emodin: Anslow, W. K. et al. *Biochem. J.* 34: 159, 1940.

6. Skyrin: Auterhoff, H. et al. *Arch. Pharm.* 295: 850, 1962; also Banks, supra from emodin bianthrone by O₂, KOH followed by HCl, thin-layer chromatography, and gel filtration.
7. Hypericin: Brockmann, supra, also Anslow, supra.
8. Hypericin monocarboxylic acid: Thompson, R. H. *Naturally Occurring Quinones,* 2nd Ed. Academic Press, London, 1971; Banks, H. J. et al., *Insect Biochem.* 3: 139, 1973; Brown, K. S., *Chem. Soc. Rev.* 4: 263, 1973; Anslow, W. K. et al., *Biochem. J.* 34: 159, 1940.
9. Hypericin dicarboxylic acid: Banks, H. J. et al., *Aust. J. Chem.* 29: 1509–1521, 1976.
10. Pseudohypericin, Banks et al., supra.
11. Emodin Anthrone. Synthesis from reduction of emodin with hydriodic acid or stannous chloride. Brockmann, H. et al. *Chem. Ber.* 90: 2302, 1957.
12. Emodin Acid Anthrone. Synthesis from emodic acid reduced with hydriodic acid; Anslow, W. K. et al. supra and Brockmann, H. et al., *Chem. Ber.* 91: 81, 1958; Jacobsen, R. A. et al., *J. Am. Chem. Soc.* 46: 1312, 1924.
13. Protohypericin: Banks et al., supra.
14. Protohypericin monocarboxylic acid, Banks et al., supra.
15. Protohypericin di-carboxylic acid, Banks et al., supra.
16. Hydroxymethyl protohypericin, Banks et al., supra.
17. Emodin bianthrone: Anslow, W. K. et al., supra.
18. Emodinic acid bianthrone: Anslow, W. K. et al., supra.
19. Emodin bianthrone dicarboxylic acid, Anslow, W. K. et al., supra.
20. Banks et al., supra.
21. Isohypericin: Steglich, W. et al., *Angew. Chem. Int. Ed. Engl.* 12: 79, 1973; Banks, et al., supra.
22. 10-peroxy-9-anthrone: Bedford, C. T., *J. Chem. Soc. C.:* 2514, 1968.
23. Penicilliopsin: Banks et al., supra.
24. Hyperico-dehydrodianthrone: Banks et al., supra.
25. Banks et al., supra.

Moreover, the AAB compounds X–XXXII (Series D) listed below are also related to hypericin and therefore expected to possess antiviral activity.

Series D

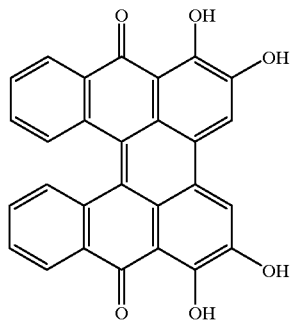

X

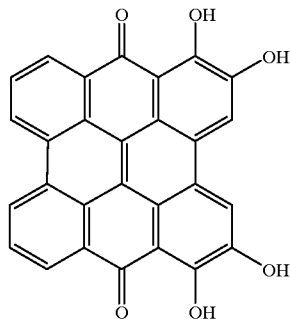

XI

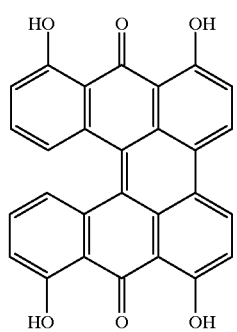

XII

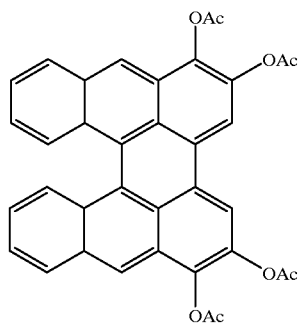

XIII

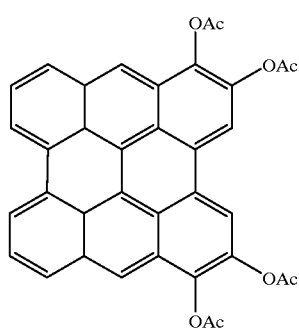

XIV

XV
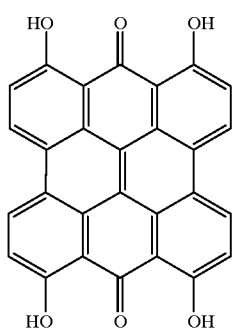
XVI
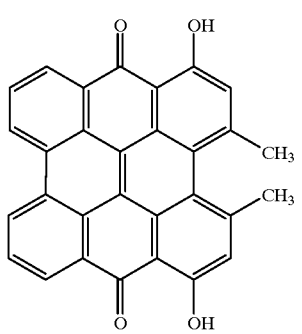
XVII
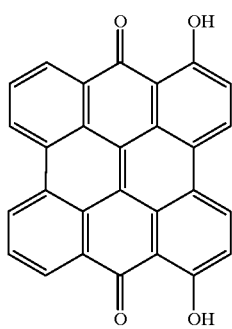
XVIII
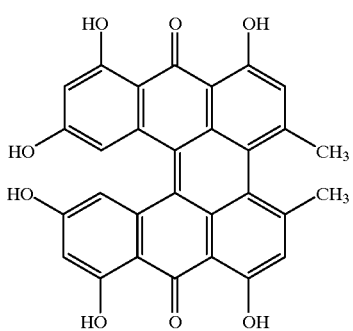
The synthesis of the above compounds has been described in Brockmann, H. M., in *Progress in Organic Chemistry*, Vol. I, Cook, J. W. ed., p.64–82, 1952.
(XIX)
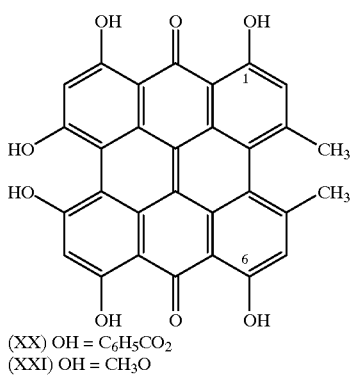
(XX) OH = $C_6H_5CO_2$
(XXI) OH = $CH_3O$
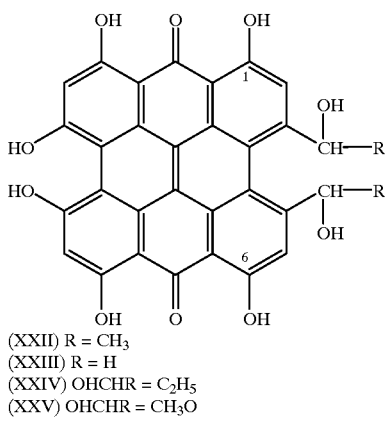
(XXII) R = $CH_3$
(XXIII) R = H
(XXIV) OHCHR = $C_2H_5$
(XXV) OHCHR = $CH_3O$
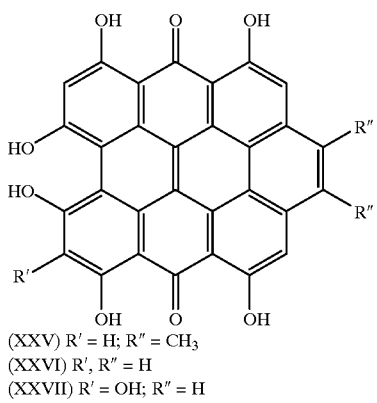
(XXV) R′ = H; R″ = $CH_3$
(XXVI) R′, R″ = H
(XXVII) R′ = OH; R″ = H
(XXVII) R′, R″, OH = H
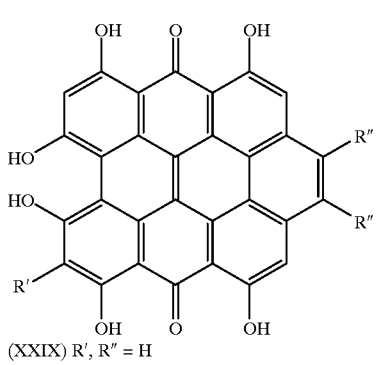
(XXIX) R′, R″ = H
(XXX) R′ = H, R″ = OH
(XXXI) R′ = OH, R″ = H
(XXXII) R′, R″ = H and OH = H at C-5

The synthesis of the above AAB compounds XIX–XXXII has been described in Brockmann, H. et al., *Tetrahedron Letters* 23: 1991–1994, 1974.

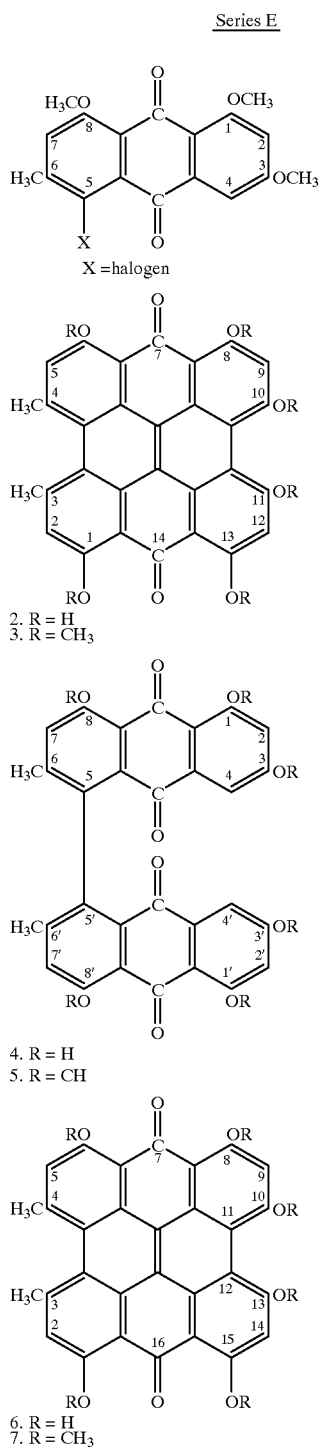

Series E

1. X = halogen
2. R = H
3. R = CH₃
4. R = H
5. R = CH
6. R = H
7. R = CH₃

The synthesis of the above compounds has been described in Brockmann, H. et al., U.S. Pat. No. 2,707,704 issued May 3, 1955.

EXAMPLE 3
Antiviral Activity of Protohypericin

The antiviral activity of the hypericin homolog protohypericin was tested as follows.

Protohypericin was synthesized by the method of Banks, H. J. et al., *Aust. J. Chem.* 29: 1509–1571, 1975. The material was purified by chromatography using silica gel 60 (mesh 0.4–0.6) and stored in the dark until use.

Supernatants (10 ml/tube) from B10.T(6R) cells (Meruelo et al. *J. Exp. Med.* 147: 470–487, 1978) chronically infected with Radiation Leukemia Virus (RadLV) were obtained by centrifugation of cells in culture at 4° C., 3500 rpm for 15 minutes. The top ⅔ of the supernatant were removed and aliquots were incubated for 30 minutes on ice with the indicated amounts of hypericin or protohypericin. The procedure was carried out in the absence of light because protohypericin converts to hypericin upon exposure to light. Thereafter, supernatants were centrifuged at 100,000×g using a TI70 rotor (Beckman Instruments) for 1 hour at 4° C. The pellet was decanted and analyzed for reverse transcriptase activity as follows.

The reverse transcriptase assay was performed in a volume of 100 microliters containing the following components:

| Reagent Stock | Microliters of Stock per assay | Final Concentration per assay |
|---|---|---|
| Sol'n A: 0.50M Tris/HCl pH 7.8 | 10 | 50 mM |
| 0.6M KCl | | 60 mM |
| Sol'n B: 2.0 mM Mn Acetate | 10 | 0.2 mM |
| Sol'n C: 40 mM dithiothreitol | 5 | 2 mM |
| Triton X-100 (10%) | 1 | 0.1% |
| poly (rA).(dT)₁₂ (10 A₂₆₀ units/ml)[1] | 4 | 0.4 A₂₆₀ units per ml |
| dTTP (2 × 10⁻⁴M) | 10 | 2 × 10⁻⁵M |
| [³H]-TTP (500 micro Ci/ml)[2] | 10 | 5 micro Ci |
| | 50 | |

[1]Obtained from Pharmacia Fine Chemical Co., (Piscataway, NJ)
[2]Obtained from New England Nuclear (Boston, MA)

The reverse transcriptase assay provides a measure of the antiviral activity of the compounds tested by reference to the observed decrease in activity of this enzyme.

The results of these assays are shown in Table V below. In Table V, "CPM" is "counts per minute", "Average" is the numerical average of CPM values within each group of animals.

TABLE V

Antiretroviral Activity of Protohypericin

| Addition (micrograms) | CPM | Average | Average percent inhibition |
|---|---|---|---|
| None (negative control) | 195,554 222,846 | 209,200 | — |
| 100 hypericin | 1,502 2,158 | 1,830 | 99.0 |
| 50 hypericin | 5,434 3,716 | 4,575 | 97.8 |
| 10 hypericin | 8,912 9,102 | 9,007 | 95.7 |
| 5 hypericin | 12,224 11,332 | 11,778 | 94.4 |
| 1 hypericin | 4,504 3,690 | 4,097 | 98.0 |
| 0.5 hypericin | 3,190 3,667 | 3,428.5 | 98.4 |
| 0.1 hypericin | 1,668 2,998 | 2,333 | 98.9 |

TABLE V-continued

Antiretroviral Activity of Protohypericin

| Addition (micrograms) | CPM | Average | Average percent inhibition |
|---|---|---|---|
| 0.05 hypericin | 2,882 | 3,067 | 98.5 |
| | 3,252 | | |
| 100 protohypericin | 8,818 | 10,281 | 95.1 |
| | 11,744 | | |
| 50 protohypericin | 75,816 | 71,641 | 65.8 |
| | 67,466 | | |
| 10 protohypericin | 202,656 | 185,539 | 11.3 |
| | 168,422 | | |
| 5 protohypericin | 12,358 | 12,633 | 94.0 |
| | 12,908 | | |
| 1 protohypericin | 192,184 | 227,614 | — |
| | 263,044 | | |
| 0.5 protohypericin | 264,710 | 257,879 | — |
| | 251,048 | | |
| 0.1 protohypericin | 216,824 | 261,083 | — |
| | 305,342 | | |
| 0.05 protohypericin | 310,952 | 309,103 | — |
| | 307,254 | | |

As can be seen from the data in Table V, protohypericin significantly inhibited the reverse transcriptase activity of RadLV, although 10 to 100 fold higher concentrations of protohypericin were required to obtain the same degree of inhibition as that obtained with hypericin. Similarly, the activity of other AAB compounds can be tested by the same assay.

EXAMPLE 4

Antiviral Activity of Hypericin Hexaacetate

The antiviral activity of hypericin hexaacetate (HHA) was tested as follows:

Hypericin hexaacetate can be synthesized by warming hypercin in the presence of excess acetic anhydride with the addition of an acid catalyst, such as sulfuric acid or boron fluoride. Alternatively a basic catalyst can be used such as fused sodium acetate, pyridine or triethylamine. See also Brockmann, H., et al., 90:2480–2491, 1957.

The antiviral activity of HHA was tested using AQR (Bach and Meruelo, *J. Exp. Med.* 160:270–285, 1984) cells chronically infected with Radiation Leukemia Virus in the reverse transcriptase assay as described in Example 3 above. The results are shown in Table VI below.

TABLE VI

Anti-retroviral Activity of Hypericin Hexaacetate

| Addition (micrograms) | CPM | Average | Average Percent Inhibition |
|---|---|---|---|
| None (Negative control) | 477,218 | 448,251 | — |
| | 419,284 | | |
| 100 Hy | 28,946 | 31,347 | 93.0 |
| | 33,748 | | |
| 50 Hy | 33,948 | 31,818 | 92.9 |
| | 29,688 | | |
| 10 Hy | 9,288 | 11,588 | 97.4 |
| | 13,888 | | |
| 2 Hy | 14,474 | 9,986 | 97.8 |
| | 5,498 | | |
| 0.4 Hy | 1,700 | 2,489 | 99.4 |
| | 3,278 | | |
| 100 HHA | 2,750 | 2,545 | 99.4 |
| | 2,340 | | |
| 50 HHA | 5,236 | 5,305 | 98.8 |
| | 5,374 | | |
| 10 HHA | 96,654 | 91,440 | 79.6 |
| | 86,226 | | |
| 5 HHA | 221,098 | 205,891 | 54.1 |
| | 190,604 | | |
| 1 HHA | 401,306 | 451,634 | — |
| | 501,962 | | |
| 0.5 HHA | 518,336 | 501,386 | — |
| | 484,356 | | |
| 0.1 HHA | 208,882 | 202,454 | 54.8 |
| | 196,026 | | |
| 0.05 HHA | 441,410 | 466,981 | — |
| | 492,552 | | |

As can be seen from the results shown in Table VI, HHA was about as active a protohypericin in inhibiting the RadLV reverse transcriptase activity.

EXAMPLE 5

Inhibition of HIV by the Compositions of the Present Invention

The activity of the AAB compounds of the present invention against human immunodeficiency virus (HIV) may be investigated in the following manner. HIV-infected cells, such as OKT4+ lymphoblastoid cells, e.g. clone H9 (described in Popovic, M., et al, *Science* 224:497–500, 1984) or HUT 78 cells (Gazdar, A F et al. *Blood* 55:409, 1980) or Molt-78 (available as ATCC CRL 1582 from the American Type Culture Collection, Rockville, Md.) are maintained in RPMI-1640 medium (GIBCO, Grand Island, N.Y.) containing 20% fetal calf serum (Flow Laboratories, Inglewood, Calif.). Triplicate cultures of cells, seeded at a concentration of about $4 \times 10^5$ cells per ml, are exposed to polybrene (2 micrograms per ml, Sigma Chemical Co., St. Louis, Mo.), infected with $2 \times 10^8$ HIV particles per $4 \times 10^5$ cells, and cultured in the presence or absence of the compounds of the present invention as in Examples 1 and 2 above.

The antiviral activity of the compounds of the present invention is determined by monitoring the reverse transcriptase activity and the expression of HIV proteins p24 and p17, as described in Sarin, P. S. et al., (*J. Nat. Cancer Inst.* 78:663–665, 1987), and as described below.

Expression of HIV GAG Proteins P24 and P17.

HUT-78, Molt-4 or H9 cells ($2 \times 10^5$), either uninfected or HIV infected, are continuously exposed to various concentrations of the compounds of the present invention at concentrations between 5 and 200 micrograms per ml for 4 days. The percentage of cells expressing p24 and p17 proteins of HIV is determined by indirect immunofluorescence microscopy with the use of mouse monoclonal antibodies to HIV p17 and p24 (available from numerous commercial sources such as those in HIV serum antibody detection kits from Abbott Labs, North Chicago, Ill., and from DuPont, Wilmington, Del.). The positive cells are visualized by treatment with fluorescein-labeled goat anti-mouse IgG (Cappell Laboratories, Cochranville, Pa.). The experiments are performed in duplicate and repeated at least three times.

Determination of Reverse Transcriptase Activity

H9, HUT-78 or MOLT-4 cells infected with HIV are exposed to various concentrations of the compounds of the present invention as above. At day 4, supernatants of the cultures are collected and virus particles are precipitated with polyethylene glycol and obtained by centrifugation as described above and assayed for reverse transcriptase activity as follows.

The virus pellet is suspended in 300 microliters of buffer containing 50 mM Tris-HCl (pH 7.5), 5 mM dithiothreitol, 250 mM KCl, and 0.25% Triton X-100. Reverse transcriptase activity in these samples are analyzed in a 50 microliter reaction mixture containing 50 mM Tris/HCl (pH 7.5), 5 mM dithiothreitol, 100 mM KCl, 0.1% Triton X-100, 10 microliters $dT_{15}rA_n$ as template primer, 10 mM $MgCl_2$, 15 micromolar [$^3$H]dTTP (New England Nuclear, Boston, Mass.), and 10 microliters of disrupted virus suspension. After incubation for 1 hour at 37° C. and subsequent addition of 50 micrograms of yeast tRNA (Sigma Chemical, St. Louis, Mo.), the incorporation of radioactivity into the cold trichloroacetic acid-insoluble fraction is assayed.

Assays are performed in duplicate and repeated three times.

EXAMPLE 6

The Effect of the Composition of the Present Invention on the Replication of Feline Leukemia Virus Cats which test positive for feline leukemia virus (FeLV) viremia will be inoculated with the compounds of the present invention (as shown in Examples 1 and 2 above), with and without nucleoside analogs, at 5–20 mg/kg twice a day for various intervals of time. Serum levels of FeLV will then be followed and treatment will be resumed using the same regimens or adjusted with respect to the levels of viremia suppression obtained. The length of follow up will be determined by experimental considerations. A minimum of six months follow-up will be undertaken.

EXAMPLE 7

Chemical Synthesis of AAB Compounds.

The following AAB compounds, referred to as WIS-1–WIS-6 were synthesized as follows below.

WIS-1-Hypericin-dicarboxylic acid.

This compound has been described by Banks, H. J. et al., Aust. J. Chem. 29: 1509–1521, 1976. Its chemical structure and synthesis are shown below.

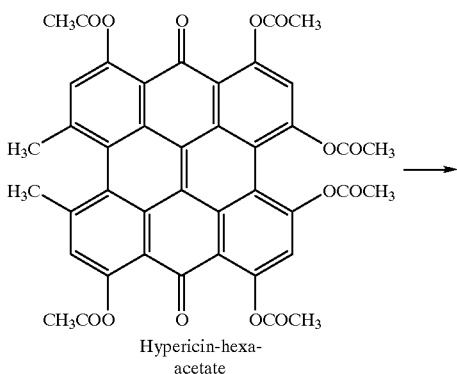
Hypericin-hexa-acetate

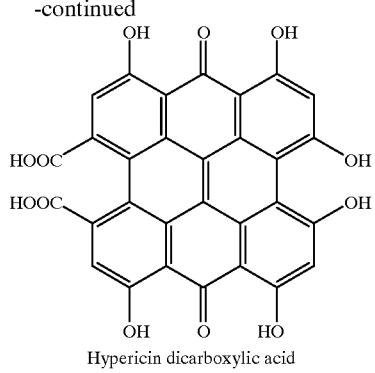
Hypericin dicarboxylic acid 200 mg hypericin hexaacetate (Brockmann, H. et al., Tetrahedron Letters: 2: 37–40, 1975) and whose synthesis is also described above in Example 4 was dissolved in 4 ml acetic acid and treated dropwise with a solution of 720 mg of chromium trioxide in 0.3 ml water and 3 ml acetic acid. After incubation for 1 hour at 55° C., the reaction mixture was poured into 50 ml of water, incubated overnight at room temperature and then filtered (Whatman qualitative No. 1 filter). The yellow solid obtained was dissolved in 400 ml of 0.2 M potassium hydroxide solution, heated with 0.2 ml piperidine, and the solution warmed to 60° C. for 10 minutes. The solution was then acidified to pH 1 with a 5% hydrochloric acid solution and the black precipitate obtained was filtered (Whatman qualitative No. 1 filter) to give the desired product.

$\lambda_{max}$ (MeOH) 600 ( 35,000), 555 (17,000), 518 (10,000) nm.[1] v(KBr) 1590, 1700 3000 $cm^{-1}$.[2] $^1$H NMR ($CD_3SO$) δ 7.72, 6.42 ppm.[3]

[1] $\lambda_{max}$=wavelength absorption peak in MeOH (=molar extinction coefficient).
[2] v=frequency, $cm^{-1}$.
[3] δ=chemical shift ppm (parts per million) as described in Spectroscopic Methods in Organic Chemistry, Williams, D. A. et al. (eds) pp. 40–129, McGraw-Hill Ltd., London, 1966.

WIS-2-Tetrahydroxy-dibenzoperylene-dione

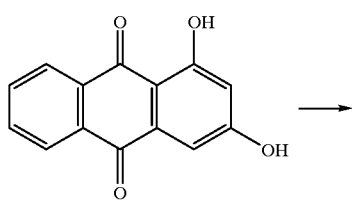

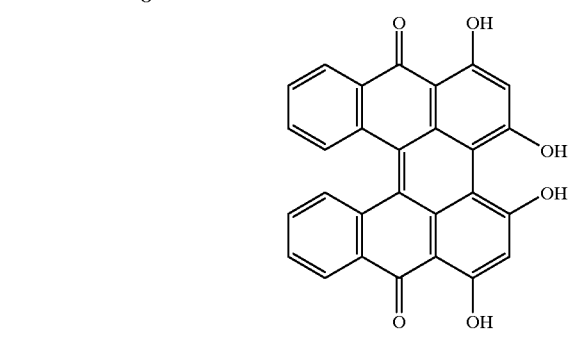

This compound has been described in Rodewald, G. et al., Angew. Chem. Int. Ed. 16: 46–47, 1977.

5 g of 1, 3-dihydroxyanthraquinone (Perkin, A. G. et al., J. Chem. Soc. 1929:1399–1411) was dissolved in 92 ml water containing 5 g of potassium tert-butoxide, and treated with 3 g hydroquinone. The resulting dark red solution was introduced into a glass ampule, purged with argon gas and then sealed. The sealed glass ampule was heated in an oil bath at 120° C. for 20 days. The contents of the ampule were then acidified with a solution of hydrochloric acid (1%) to pH 1, extracted with a solution of butanol and ethyl acetate (1:1), washed with distilled water until neutral and evaporated to dryness. The residue obtained was chromatograph on a column of silica gel and eluted with a mixture of ethyl acetate:butanol (100:5) to yield 350 mg of the product which did not change upon irradiation. The physical data (lambda$_{max}$, $^1$H NMR) were identical to those reported in the above-cited Rodewald et al. publication.

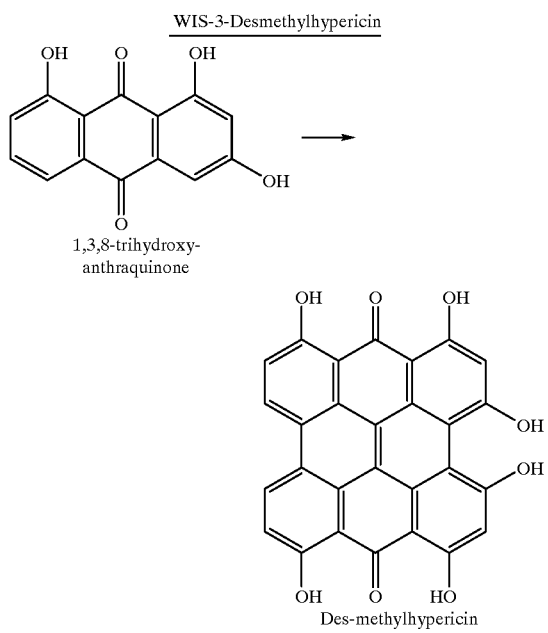

This compound has been previously described and characterized (Cameron, D. W. et al., *Aust. J. Chem.* 29:1523–1533, 1976).

1, 3, 8-Trihydroxyanthraquinone (300 mg) (prepared as described in Lovie, J. C. et al., *J. Chem. Soc.* 1961:485–486) was dissolved in 10 ml water containing 0.5 g of potassium tert-butoxide, and treated with 0.3 g hydroquinone. The resulting dark red solution was introduced into a glass ampule which was purged with argon gas, and then sealed. The sealed glass ampule was incubated in an oil bath at 140° C. for 21 days. The contents were then acidified with a solution of hydrochloric acid (1%) to pH 1, extracted with a solution of butanol and ethyl acetate (1:1), washed with distilled water until neutral and evaporated to dryness. The residue was chromatographed on a column of silica gel and eluted with a mixture of ethyl acetate:methanol (100:5) yielding a desmethyl analog of protohypericin in the amount of 50 mg. This material was dissolved in ethyl acetate and irradiated with visible light for one hour. The solvent was evaporated to dryness resulting in desmethylhypericin in a yield of 44 mg. The compound was a dark red amorphous solid.

λ$_{max}$ (in MeOH): 580 (45,000), 537 (25,000), 502 (15,000), 468 (30,000) nm. ν$_{max}$ (KBr): 3400, 1620, 1590, 1550. $^1$H NMR (CD$_3$SO) δ8.48 (d, J=8H), 7.15(d, J=8HZ), 6.57 (s) ppm

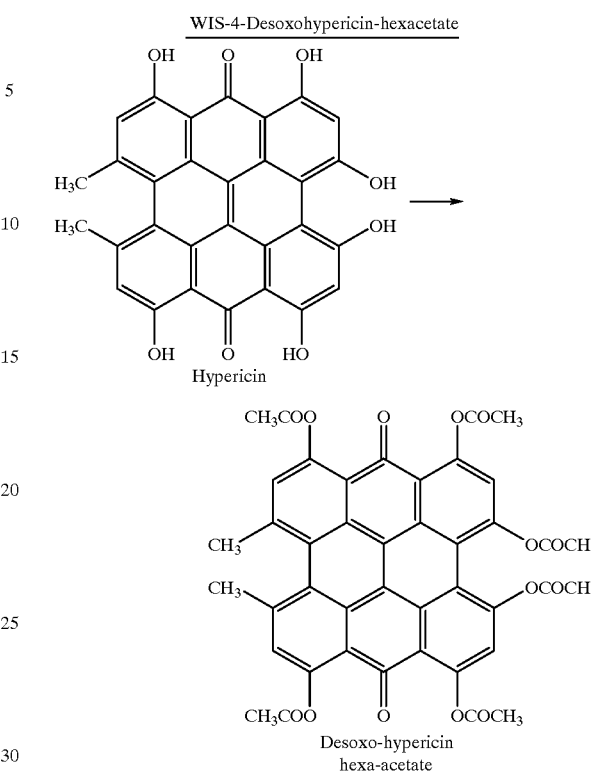

This compound has been previously disclosed in Brockmann, H. et al., *Chem. Ber.* 90: 2481–2491, 1957.

200 mg hypericin and 200 mg sodium acetate were heated over reflux for 10 minutes and treated with 4 g zinc powder, added in small portions. The residue was filtered (Whatman qualitative No. 1 filter) dried, dissolved in 50 ml benzene and filtered again. The solution thus obtained was treated with 275 mg chloranil, boiled under reflux for 30 minutes and incubated for 2 days at room temperature. The dark blue solution was filtered through a column containing 50 g of silica gel. The reaction product was eluted with a mixture of benzene and acetone (100:2) yielding 55 mg of desoxohypericinhexaacetate.

UV (in MeOH) 621 (45,000), 567 (24,000), 310 (91,000) nm. $^1$H NMR (CDCl$_3$)δ2.36, 2.40, 2.45, 2.46, 8.3, 7.44, 7.39 ppm.

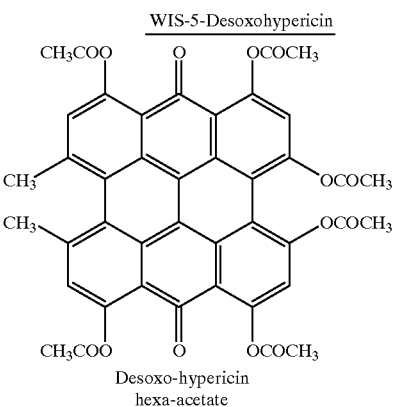

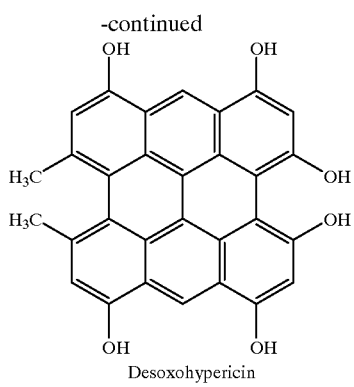

Desoxohypericin

This is a new compound not previously described in the literature which was prepared by hydrolysis of desoxoyhypericin-hexaacetate (WIS-4).

20 mg of desoxoyhypericin-hexaacetate (synthesized as described above) was dissolved in 8 ml ethanol containing 20 mg sodium hydroxide. The solution was incubated at room temperature for 24 hours. After this period, all of the acetate groups were hydrolyzed yielding the sodium salt of desoxyhypericin. The material was not isolated from solutions since it decomposses readily in neutral or acetic pH. UV (ethanol, pH 10) λ max >800, 755, 438 nm.

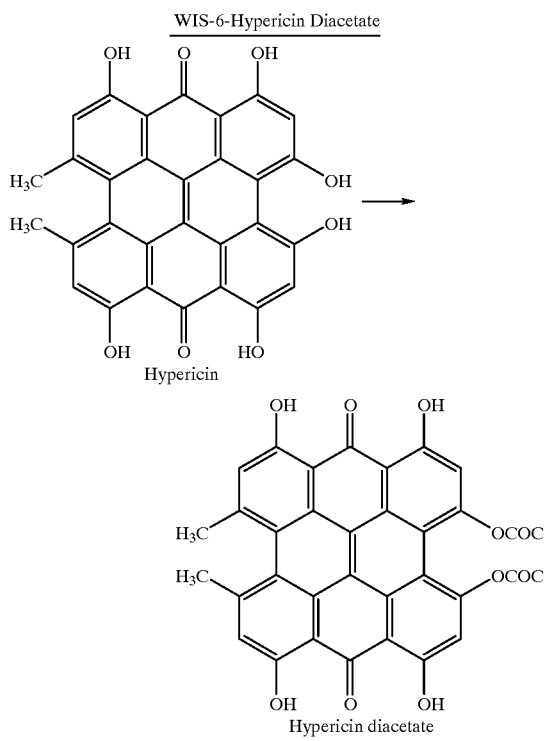

This compound has been described in Brockmann, H. et al., *Chem. Ber.* 84: 865–867, 1951.

200 mg hypericin was dissolved in 50 ml acetic anhydrive and incubated at room temperature for 48 hours. It was then poured over ice and extracted with 100 ml ethyl acetate. The organic extract was washed with 50 ml of a dilute hydrochloric acid solution (1%) and 500 ml sodium bicarbonate (3%). The residue, after evaporation of the organic solvent, was chromatographed over silica gel. The fraction eluted with ethyl acetate and comprised orange crystals of hypericin diacetate with a melting point higher than 360° C.

$\lambda^{max}$ (MeOH) 586 (35,000), 573 (25,000), 544 (20,000), 458 (28,000), 434 (18000) nm. $^1$H NMR (in CDCl$_3$) δ 2.39, 2.82, 7.28 ppm.

EXAMPLE 8

Biological Activity

The AAB compounds whose synthesis is described above were assayed for antiviral activity. WIS-2, -3, -4, -5 and -6 were tested to determine their biological effects on Friend Virus-induced splenomegaly using the procedure and technique set forth in Example 1 above. The assay results (three mice per group were tested each at different concentrationss of the active composition except for the PBS-negative control wherein two animals per group were used) are reported in Table VII below.

TABLE VII

| TREATMENT | Actual Spleen Weight | Average Spleen Weight | Average % Inhibition |
|---|---|---|---|
| PBS (negative control) | 0.1947 | 0.1754 | — |
|  | 0.1460 |  |  |
| FV (positive control) | 0.9484 | 0.9661 | — |
|  | 0.9826 |  |  |
|  | 0.9673 |  |  |
| WIS-2 (150 micrograms) | 0.4075 | 0.4416 | 66.3 |
|  | 0.4656 |  |  |
|  | 0.4517 |  |  |
| WIS-2 (50 micrograms) | 0.4818 | 0.4603 | 64.0 |
|  | 0.4925 |  |  |
|  | 0.4066 |  |  |
| WIS-2 (10 micrograms) | 0.4263 | 0.4701 | 62.7 |
|  | 0.4868 |  |  |
|  | 0.4972 |  |  |
| WIS-2 (1 microgram) | 0.6615 | 0.7015 | 53.9 |
|  | 0.7519 |  |  |
|  | 0.6912 |  |  |
| WIS-3 (150 micrograms) | 0.2967 | 0.3290 | 79.7 |
|  | 0.3518 |  |  |
|  | 0.3384 |  |  |
| WIS-3 (50 micrograms) | 0.6998 | 0.6921 | 34.7 |
|  | 0.6723 |  |  |
|  | 0.7041 |  |  |
| WIS-3 (10 micrograms) | 0.7727 | 0.7759 | 24.1 |
|  | 0.8108 |  |  |
|  | 0.7413 |  |  |
| WIS-3 (1 microgram) | 0.7527 | 0.7737 | 24.3 |
|  | 0.8048 |  |  |
|  | 0.7277 |  |  |
| WIS-4 (150 micrograms) | 0.6214 | 0.6012 | 46.1 |
|  | 0.6663 |  |  |
|  | 0.5159 |  |  |
| WIS-4 (50 micrograms) | 0.7368 | 0.7384 | 28.8 |
|  | 0.7744 |  |  |
|  | 0.7041 |  |  |
| WIS-4 (10 micrograms) | 0.8118 | 0.7921 | 22.0 |
|  | 0.8625 |  |  |
|  | 0.7019 |  |  |
| WIS-4 (1 microgram) | 0.7790 | 0.8480 | 14.9 |
|  | 0.8852 |  |  |
|  | 0.8797 |  |  |
| WIS-5 (150 micrograms) | 0.6919 | 0.6879 | 35.2 |
|  | 0.6790 |  |  |
|  | 0.6927 |  |  |
| WIS-5 (50 micrograms) | 0.7817 | 0.8134 | 19.3 |
|  | 0.8389 |  |  |
|  | 0.8196 |  |  |
| WIS-5 (10 micrograms) | 0.9126 | 0.9147 | 6.5 |
|  | 0.8898 |  |  |
|  | 0.9417 |  |  |
| WIS-5 (1 microgram) | 0.9062 | 0.9197 | 5.9 |
|  | 0.9528 |  |  |
|  | 0.9001 |  |  |
| WIS-6 (150 micrograms) | 0.7921 | 0.8187 | 18.6 |
|  | 0.8013 |  |  |
|  | 0.8626 |  |  |

TABLE VII-continued

| TREATMENT | Actual Spleen Weight | Average Spleen Weight | Average % Inhibition |
|---|---|---|---|
| WIS-6 (50 micrograms) | 0.9012 | 0.9407 | 3.2 |
|  | 0.9969 |  |  |
|  | 0.9241 |  |  |
| WIS-6 (10 micrograms) | 0.8387 | 0.8930 | 9.2 |
|  | 0.8529 |  |  |
|  | 0.9874 |  |  |
| WIS-6 (1 microgram) | 0.9291 | 0.8210 | 18.4 |
|  | 0.8017 |  |  |
|  | 0.7323 |  |  |

Referring to Table VII above, it can be seen that all of the analogs demonstrated antiviral activity. WIS-2, 3, and 4 were the most active compounds of the group in the splenomegaly assay.

EXAMPLE 9

Radiation Leukemia Virus Reverse Transcriptase Assay

The same group of analog compounds used in Example 8 were tested to determine their ability to directly inhibit the reverse transcriptase of Radiation Leukemia Virus. The assays were conducted using the same procedure as in Example 3 above, using supernatants from infected AQR cells. The results of the assay are reported below in Table VIII.

TABLE VIII

| Treatment | CPM | Average | Average % Inhibition |
|---|---|---|---|
| None (negative control) | 829,640 | 816,568 |  |
|  | 803,496 |  |  |
| WIS-2 (10 micrograms) | 4,158 | 4,156 | 99.5 |
|  | 4,154 |  |  |
| WIS-2 (5 micrograms) | 4,278 | 3,922 | 99.5 |
|  | 3,566 |  |  |
| WIS-2 (2 micrograms) | 4,100 | 4,343 | 99.5 |
|  | 4,586 |  |  |
| WIS-2 (1 microgram) | 11,576 | 10,503 | 98.7 |
|  | 9,430 |  |  |
| WIS-2 (0.5 micrograms) | 16,602 | 15,306 | 98.1 |
|  | 14,010 |  |  |
| WIS-2 (0.1 micrograms) | 212,984 | 238,201 | 70.8 |
|  | 263,418 |  |  |
| WIS-2 (0.05 micrograms) | 455,360 | 476,704 | 41.6 |
|  | 498,048 |  |  |
| WIS-3 (10 micrograms) | 57,512 | 119,248 | 85.4 |
|  | 61,736 |  |  |
| WIS-3 (5 micrograms) | 75,776 | 76,907 | 90.6 |
|  | 78,038 |  |  |
| WIS-3 (2 micrograms) | 14,020 | 15,467 | 98.1 |
|  | 16,914 |  |  |
| WIS-3 (1 microgram) | 21,896 | 24,606 | 97.0 |
|  | 27,316 |  |  |
| WIS-3 (0.5 micrograms) | 2,630 | 2,799 | 99.7 |
|  | 2,968 |  |  |
| WIS-3 (0.1 micrograms) | 19,322 | 20,893 | 97.4 |
|  | 22,464 |  |  |
| WIS-3 (0.05 micrograms) | 89,170 | 78,424 | 90.4 |
|  | 67,678 |  |  |
| WIS-4 (10 micrograms) | 186,168 | 184,852 | 77.4 |
|  | 183,536 |  |  |
| WIS-4 (5 micrograms) | 164,780 | 164,440 | 79.9 |
|  | 164,100 |  |  |
| WIS-4 (2 micrograms) | 236,374 | 237,365 | 70.9 |
|  | 238,356 |  |  |
| WIS-4 (1 microgram) | 179,312 | 180,180 | 77.9 |
|  | 181,048 |  |  |
| WIS-4 (0.5 micrograms) | 196,740 | 208,119 | 74.5 |
|  | 219,498 |  |  |
| WIS-4 (0.1 micrograms) | 100,504 | 144,512 | 82.3 |
|  | 188,520 |  |  |
| WIS-4 (0.05 micrograms) | 156,830 | 164,212 | 79.9 |
|  | 171,594 |  |  |
| WIS-5 (10 micrograms) | 168,008 | 177,364 | 78.3 |
|  | 186,720 |  |  |
| WIS-5 (5 micrograms) | 220,588 | 236,878 | 71.0 |
|  | 253,168 |  |  |
| WIS-5 (2 micrograms) | 216,764 | 205,469 | 74.8 |
|  | 194,174 |  |  |
| WIS-5 (1 microgram) | 238,782 | 251,168 | 69.2 |
|  | 263,554 |  |  |
| WIS-5 (0.5 micrograms) | 240,372 | 249,351 | 69.5 |
|  | 258,330 |  |  |
| WIS-5 (0.1 micrograms) | 172,984 | 171,635 | 79.0 |
|  | 170,286 |  |  |
| WIS-5 (0.05 micrograms) | 183,654 | 193,017 | 76.4 |
|  | 202,380 |  |  |
| WIS-6 (10 micrograms) | 178,026 | 146,588 | 82.0 |
|  | 115,150 |  |  |
| WIS-6 (5 micrograms) | 86,850 | 90,273 | 88.9 |
|  | 93,696 |  |  |
| WIS-6 (2 micrograms) | 96,562 | 94,199 | 88.5 |
|  | 91,836 |  |  |
| WIS-6 (1 microgram) | 124,996 | 153,363 | 81.2 |
|  | 181,730 |  |  |
| WIS-6 (0.5 micrograms) | 116,590 | 161,570 | 80.2 |
|  | 206,550 |  |  |
| WIS-6 (0.1 micrograms) | 188,378 | 389,388 | 52.3 |
|  | 590,398 |  |  |
| WIS-6 (0.05 micrograms) | 195,374 | 190,506 | 76.7 |
|  | 185,638 |  |  |

The assay results in Table VIII above showed that all of the compounds tested were found to inhibit the reverse transcriptase activity of Radiation Leukemia Virus. Compounds WIS-2 and WIS-3 had the highest level of antiviral activity of the compounds that were tested in this assay.

EXAMPLE 10

In order to investigate the structural features of hypericin which are essential for antiretroviral activity, numerous analogs and precursors of hypericin were examined for activity in two in vitro and one in vivo biological assay.

The assays employed were:
(1) Direct inactivation of retroviruses in vitro, performed as in Example 3 above;
(2) In vitro inhibition of a virus budding, performed as described in Meruelo, D. et al. (Proc. Natl. Acad. Sci. USA 85: 5230–5234, 1988 and Lavie G. et al. (Proc. Natl. Acad. Sci. USA 86: 5963–5967, 1989). Briefly, tissue culture adapted, virus-producing cells were incubated with various amounts of compounds for 30 minutes at 37° C. After 30 minutes the cells were washed three times with Dulbecco's Modified Eagle Medium (DMEM) supplemented with fetal calf serum, growth factors and antibiotics and cultured for 24 to 48 hours. The cells were then harvested and the culture supernatants were assayed for reverse transcriptase activity as described above in Example 3;
(3) In vivo inhibition of Friend Leukemia Virus Splenomegaly performed as described in Example 1 above except that the compounds were administered intravenously 1–2 hours post infection.

The synthesis and/or isolation of these compounds is described above.

The results of these assays are presented in Table IX below.

TABLE IX

| COMPOUND | EC$_{50}$ (uM) FOR DIRECT INACTIVATION OF VIRIONS | EC$_{50}$ (uM) FOR PRODUCTION OF DEFECTIVE BUDDED VIRIONS | EC$_{50}$ (uM) FOR FV-INDUCED SPLENOMEGALY |
|---|---|---|---|
| HYPERICIN | 0.06 | 0.2 | 0.12 |
| PROTOHYPERICIN | 7.90 | — | 98 |
| PSEUDOHYPERICIN | — | — | 3.8 |
| HYPERICIN-DICARBOXYLIC-ACID (WIS-1) | — | >100 | — |
| HYPERICIN-DIACETATE (WIS-6) | 0.85 | — | >255 |
| HYPERICIN-HEXAACETATE | 12.90 | — | >199 |
| DESMETHYL-HYPERICIN (WIS-3) | 0.07 | 2 | 174 |
| DESOXOHYPERICIN (WIS-5) | >21 | — | >316 |
| DESOXOHYPERICIN-HEXAACETATE (WIS-4) | 6.90 | — | >242 |
| EMODIN | >37 | — | — |
| HYDROXYMETHYL-ANTHRAQUINONE | >41 | — | 145 |
| ANTHRONE | >51 | — | 267 |
| BIANTHRONE | >26 | >100 | 98 |

The results presented above in Table IX are presented as EC$_{50}$ concentrations. These are the effective concentrations which inhibit 50% of the viruses in micromolar concentrations.

As can be seen from the results presented in Table IX above, different analogs varied in their levels of effectiveness. Only hypericin, pseudohypericin and desmethyl hypericin showed a high degree of activity in a more than one assay. Removal of the carbonyl groups from hypericin (e.g., desoxohypericin) resulted in a significant loss of in vivo reverse transcriptase inhibitory activity. This loss of activity was also evident when the activities of the hexaacetate derivative of hypericin are compared with those of the desoxo-hexaacetate derivative. These observations suggest that the quinone structure was important for the antiviral activity of aromatic polycyclic diones, preferably when structured on a naphthodianthrone backbone. In addition, replacement of the methyl side chains by a more polar group such as a carboxylic, acetoxy, or hydroxy side group diminished the antiviral activity as seen above in hypericin dicarboxylic acid and the di-and hexaacetate derivatives of hypericin.

What is claimed is:

1. A method for treating a mammal suffering from a viral infection comprising administering to a mammal in need of such treatment an amount effective to provide a significant inhibition of the virus causing said viral infection of a compound having antiviral activity of the following formula (I):

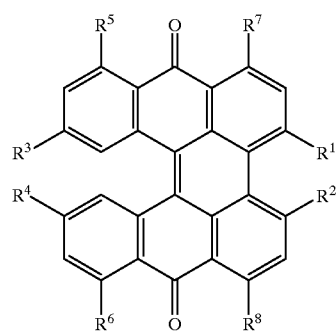

wherein $R^1$ and $R^2$ are OH, $R^3$ and $R^4$ are H, $R^5$ and $R^6$ are H, and $R^7$ and $R^8$ are OH.

2. A pharmaceutical composition for treating mammals suffering from viral infections comprising a pharmaceutically acceptable carrier or diluent and, as active principle, an antiviral effective amount of a compound having antiviral activity of the following formula (I):

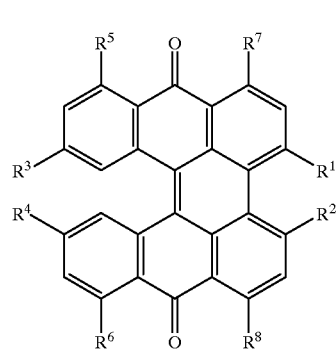

wherein $R^1$ and $R^2$ are OH, $R^3$ and $R^4$ are H, $R^5$ and $R^6$ are H, and $R^7$ and $R^8$ are OH.

* * * * *